US010004824B2

(12) United States Patent
Vitally et al.

(10) Patent No.: US 10,004,824 B2
(45) Date of Patent: Jun. 26, 2018

(54) COMPOSITIONS COMPRISING AT LEAST ONE POLYOL AND AT LEAST ONE ANESTHETIC

(71) Applicant: LABORATOIRES VIVACY, Archamps (FR)

(72) Inventors: Guy Vitally, Le Bourget du Lac (FR); Jérémie Bon Betemps, Albens (FR)

(73) Assignee: LABORATOIRES VIVACY, Archamps (FR)

( * ) Notice: Subject to any disclaimer, the term of this patent is extended or adjusted under 35 U.S.C. 154(b) by 0 days. days.

(21) Appl. No.: 14/708,776

(22) Filed: May 11, 2015

(65) Prior Publication Data

US 2016/0331865 A1 Nov. 17, 2016

(51) Int. Cl.
  *A61L 27/20* (2006.01)
  *A61L 27/54* (2006.01)
  *A61L 27/58* (2006.01)

(52) U.S. Cl.
  CPC .............. *A61L 27/20* (2013.01); *A61L 27/54* (2013.01); *A61L 27/58* (2013.01); *A61L 2300/402* (2013.01); *A61L 2400/06* (2013.01); *A61L 2430/34* (2013.01)

(58) Field of Classification Search
  CPC .......... A61L 27/20; A61L 27/54; A61L 27/58; A61L 2300/402; A61L 2400/06; A61L 2430/34
  See application file for complete search history.

(56) References Cited

U.S. PATENT DOCUMENTS

| 5,087,446 | A | 2/1992 | Suzuki et al. |
| 5,827,937 | A | 10/1998 | Agerup |
| 7,838,551 | B2 * | 11/2010 | Santini ................ A61K 9/0019 514/408 |
| 8,124,120 | B2 | 2/2012 | Sadozai et al. |
| 9,314,530 | B2 | 4/2016 | Piron et al. |
| 2002/0019339 | A1 | 2/2002 | Naughton |
| 2006/0122147 | A1 | 6/2006 | Wohlrab |
| 2006/0194758 | A1 | 8/2006 | Lebreton |
| 2007/0077292 | A1 | 4/2007 | Pinsky |
| 2010/0028437 | A1 | 2/2010 | Lebreton |
| 2010/0255068 | A1 | 10/2010 | Stroumpoulis et al. |
| 2010/0303873 | A1 | 12/2010 | Piron et al. |
| 2010/0316683 | A1 | 12/2010 | Piron et al. |
| 2011/0201571 | A1* | 8/2011 | Gavard Molliard . A61K 9/0024 514/54 |
| 2011/0230438 | A1 | 9/2011 | Bos |
| 2012/0004292 | A1 | 1/2012 | Villette |
| 2012/0108674 | A1 | 5/2012 | Gavard Molliard et al. |
| 2013/0089579 | A1 | 4/2013 | Laeschke |
| 2013/0172288 | A1 | 7/2013 | Bon Betemps et al. |
| 2013/0274224 | A1 | 10/2013 | Gavard Molliard |
| 2014/0005140 | A1 | 1/2014 | Piron et al. |
| 2014/0088037 | A1 | 3/2014 | Bon Betemps et al. |
| 2014/0378411 | A1 | 12/2014 | Ragg |
| 2015/0038457 | A1 | 2/2015 | Bourdon et al. |

FOREIGN PATENT DOCUMENTS

| CN | 102805882 A | 12/2012 |
| CN | 102949755 A | 3/2013 |
| EP | 0 466 300 A2 | 1/1992 |
| EP | 1 837 347 A1 | 9/2007 |
| EP | 2 349 203 BI | 8/2011 |
| EP | 2 404 619 A1 | 1/2012 |
| EP | 2 484 387 A1 | 8/2012 |
| EP | 2 581 079 A1 | 4/2013 |
| FR | 2 938 187 A1 | 5/2010 |
| FR | 2 979 539 A1 | 3/2013 |
| FR | 2979539 A1 | 3/2013 |
| FR | 2 983 483 A1 | 6/2013 |
| FR | 2983483 A1 | 6/2013 |
| KR | 2014/0025117 A | 3/2014 |
| WO | 8600079 A1 | 1/1986 |
| WO | 1993/012801 A1 | 7/1993 |
| WO | 98/41171 A1 | 9/1998 |
| WO | 00/46253 A1 | 8/2000 |

(Continued)

OTHER PUBLICATIONS

Belda, Jose I. et al., "Hyaluronic acid combined with mannitol to improve protection against free-radical endothelial damage: Experimental Model", Belda-Journal of cataract and refractive surgery, (2005), 31. 1213-1218.

Wahl, Gregor, European evaluation of a new hyaluronic acid filler incorporating lidocaine, 2008, Journal of Cosmetic Dermatology, 7, 298-303.

Gold, Michael H., "Use of Hyaluronic Acid Fillers for the Treatment of the Aging Face", Clinical Interventions in Aging, vol. 2(3), pp. 369-376, 2007.

Cho, Cheong-Weon, et al., "Enhanced Local Anesthetic Action of Mepivacaine From the Bioadhesive Gels", Pak. J. Pharm. Sci., vol. 24, No. 1, pp. 87-93, 2011.

Daithankar, Aarti V., et al., "Thermoreversibal Anesthetic Gel for Periodontal Intrapocket Delivery of Mepivacaine Hydrochloride", Der Pharmacia Lettre, vol. 4-3, pp. 889-896, 2012.

Christoph, Richard A., MD, et al., "Pain Reduction in Local Anesthetic Administration Through pH Buffering", Annals Emerg Medicine, vol. 17-2, pp. 117-120, 1988.

McGlone, R., et al., "Reducing the Pain of Intradermal Lignocaine Injection by pH Buffering", Archives of Emergency Medicine, vol. 7, pp. 65-68, 1990.

Shandler, Lawrence, "Mechanism of Action of Local Anesthetics", Journal of the American Dental Society of Anesthesiology, pp. 62-66, 1965.

(Continued)

*Primary Examiner* — Sahar Javanmard
(74) *Attorney, Agent, or Firm* — Oliff PLC

(57) ABSTRACT

An injectable sterilized aqueous composition including at least one hyaluronic acid, at least one polyol and at least one local anesthetic chosen from the group made of benzocaine, chloroprocaine, procaine, etidocaine, aptocaine, chlorobutanol, diamocaine, dyclonine, guafecainol, polidocanol, mepivacaine, prilocaine, articaine, bupivacaine, ropivacaine, tetracaine and salts thereof and isolated isomers thereof. The invention also relates to a process for adapting the rheological properties of a heat sterilized injectable aqueous composition. The invention also relates to a process for producing an injectable sterilized aqueous composition according to the invention, and also to uses of said injectable sterilized aqueous composition according to the invention.

14 Claims, No Drawings

(56) References Cited

FOREIGN PATENT DOCUMENTS

| | | |
|---|---|---|
| WO | 2004/032943 A1 | 4/2004 |
| WO | 2004/073759 A1 | 9/2004 |
| WO | 2004/092222 A2 | 10/2004 |
| WO | 2005/067994 A1 | 7/2005 |
| WO | 2005/072751 A1 | 8/2005 |
| WO | 2005/112888 A2 | 12/2005 |
| WO | 2006/067608 A1 | 6/2006 |
| WO | 2006/073835 A2 | 7/2006 |
| WO | 2007/128923 A2 | 6/2007 |
| WO | 2007/077399 A2 | 7/2007 |
| WO | 2008/068297 A1 | 6/2008 |
| WO | 2009/071697 A1 | 6/2009 |
| WO | 2010/015901 A1 | 1/2010 |
| WO | 2010/052430 A2 | 3/2010 |
| WO | 2010/131175 A1 | 11/2010 |
| WO | 2010/136694 A2 | 12/2010 |
| WO | 2011/086458 A1 | 7/2011 |
| WO | 2012/080915 A1 | 6/2012 |
| WO | 2012/104419 A1 | 8/2012 |
| WO | 2012/143876 A1 | 10/2012 |
| WO | 2014/056722 A2 | 6/2013 |
| WO | 2013/186493 A2 | 12/2013 |
| WO | 2014/032804 A1 | 3/2014 |
| WO | 2013/092860 A2 | 4/2014 |
| WO | 2014/056722 A2 | 4/2014 |
| WO | 2015/015407 A1 | 2/2015 |
| WO | 2015/097261 A1 | 7/2015 |

OTHER PUBLICATIONS

Farley, Jon S., M.D., et al., "Diluting Lidocaine and Mepivacaine in Balanced Salt Solution Reduces the Pain of Intradermal Injection", Regional Anaesthesia, vol. 19, pp. 48-51, 1994.
Collins, Vincent J., M.D., et al., "Clinical Evaluation of Mepivacaine for Regional Anesthesia", Archives of Surgery, vol. 84, pp. 680-685, 1962.
Duranti, Fabrizio, MD, et al., "Injectable Hyaluronic Acid Gel for Soft Tissue Augmentation", Dermatologic Surgery, vol. 24, pp. 1317-1325, 1998.
Palmieri, Beniamino, Prof., "Hyaluronic Acid, Mesotherapy and Skin Rejuvenation", 2010.
Jun. 13, 2017 Office Action issued in U.S. Appl. No. 14/708,776.
U.S. Appl. No. 15/138,773, filed Apr. 26, 2016 which is a National Phase of International Application No. PCTEP201407927.
Johansson, A., et al., "Effects of Adjuvants to Local Anaesthetics on Their Duration", Acta Anaesthesiol Scand, vol. 29-7, pp. 736-738, 1985.
Sundaram, Hema, MD, et al., "Comparison of the Rheological Properties of Viscosity and Elasticity in Two Categories of Soft Tissue Fillers: Calcium Hydroxylapatite and Hyaluronic Acid", Dermatol. Surg., vol. 36, pp. 1859-1865, 2010.
Kablik, Jeffrey, et al., "Comparative Physical Properties of Hyaluronic Acid Dermal Fillers", Dermatol. Surg., vol. 35-1, pp. 302-312, 2009.
McLure, H. A., et al., "Review of Local Anaesthetic Agents", Minerva Anestesiol, vol. 71, pp. 59-74, 2005.
Cousins, Michael J., et al., "Neural Blockade in Clinical Anesthesia and Pain Medicine", 4th Ed., Wolters Kluwer, Lippicott, Chapter 3, 2008.
Domingo, et al., "Local Anesthetics: Review of Pharmacologic Aspects and Clinical Properties", Clinical Update, vol. 24, No. 9, pp. 18-20, 2002.
Sep. 21, 2017 Office Action issued in U.S. Appl. No. 15/138,773.
Mendoza et al., "Inhibitory effects of different antioxidants on hyaluronan depolymerization," Carbohydrate Research 342 (2007), pp. 96-102.
Lambers et al; "Natural skin surface pH is on average below 5, which is beneficial for its resident flora"; 2006; Int. J. Cos met. Sci.; (5): 359-70; PubMed abstract; PMID: 18489300.
Bhal; http://blog.acdlabs.com/acdlabs/2016 /07 /partitioning -logp- or -logd-are-you -using -measuring -the-right descriptor.html, accessed May 4, 2017.

* cited by examiner

COMPOSITIONS COMPRISING AT LEAST ONE POLYOL AND AT LEAST ONE ANESTHETIC

The invention relates to the field of biodegradable gels and hydrogels used as biomaterials and more particularly in the medical and aesthetics fields.

Hyaluronic acid has been used for more than fifteen years in the aesthetics field, where it has proved to be harmless and effective. At present, in the market of esthetic filling gels or fillers, gels based on crosslinked hyaluronic acid originating from biofermentation are the most widely used.

Among the medical applications, mention will for example be made of injections for replacing biological fluids that are deficient for example in joints in order to replace synovial fluid, injection following a surgery in order to prevent peritoneal adhesions, periurethral injections for treating incontinence and injections following surgery for long-sightedness.

Among the aesthetics applications, mention will for example be made of injections for filling wrinkles, fine lines or skin defects or increasing volumes, for example the lips, the cheekbones, etc.

Use of hyaluronic acid originating from biofermentation in fields such as the filling of wrinkles, viscosupplementation, ophthalmic treatment or else the treatment of urinary incontinence is acknowledged and appreciated all the more since, owing to its natural presence in the human body, and more particularly in the dermis, synovial fluid and vitreous body, the risks due to side effects are minimized.

Numerous patent applications or publications have been filed or published on hyaluronic acid-based compositions comprising, in addition to the hyaluronic acid, active agents or excipients for modifying or improving the properties of the composition according to the particular applications.

For example, application WO 2013/186493 discloses hyaluronic acid compositions including a sucrose octasulfate and application WO 2014/032804 discloses hyaluronic acid compositions including a vitamin C derivative.

Likewise, hyaluronic acid-based compositions comprising a polyol are described in the prior art.

In application WO 2007/077399 in the name of Anteis, compositions for dermatological use based on hyaluronic acid or a salt thereof and on a polyol are presented. The addition of polyol has the effect of limiting the degradation of the rheological properties of the compositions during sterilization with moist heat.

Application WO 2008/068297 in the name of Pierre Fabre Dermo Cosmetique describes protective effects, in particular in vivo, of the addition of mannitol to hyaluronic acid compositions.

Application WO 2007/128923, in the name of Anteis describes the preparation of a biocompatible gel comprising glycerol.

Application WO 2010/136694 in the name of Anteis discloses an injectable composition based on crosslinked hyaluronic acid, containing glycerol, the composition being sterilized by moist heat.

Finally, the publication "Hyaluronic acid combined with mannitol to improve protection against free-radical endothelial damage: Experimental Model" (Belda-Journal of cataract and refractive surgery (2005)-31, 1213-1218 provides details of the effects, in particular the in vivo effects, of the addition of mannitol to hyaluronic acid-based compositions.

It is, moreover, known practice to add local anesthetics to filling products in order to limit injection pain.

Certain patent applications and publications thus relate to hyaluronic acid-based compositions comprising lidocaine.

Application WO 93/12801 in the name of Reinmuller describes gels for treating wounds and cheloid scars by subcutaneous injection. Example 1 of said application relates to a composition based on hyaluronic acid of "hylagel" type (Biomatrix), and containing lidocaine.

The article by G. Wahl in Journal of Cosmetic Dermatology, relates to the incorporation of lidocaine into filling compositions based on hyaluronic acid. The results presented relate to tests carried out using Juvederm Ultra® which is a filling product based on crosslinked hyaluronic acid. According to this article, more than 87% of patients have indicated that they experience less pain during the injection of compositions incorporating lidocaine.

Application FR 2 979 539 in the name of Teoxane also discloses a hyaluronic acid-based composition comprising lidocaine.

Finally, a certain number of hyaluronic acid-based products comprising lidocaine are sold, for example Juvederm®, Restylane®, Emervel Lidocaine®, Teosyal Sense®, etc.

Anesthetics other than lidocaine are also used, for example a patent application EP 2 581 079 in the name of Biopolymer describes compositions based on hyaluronic acid and on prilocaine, which have a quick prilocaine release profile.

In application WO 2015/015407 in the name of Teoxane, compositions based on non-crosslinked and partially crosslinked hyaluronic acid comprising mepivacaine and lidocaine are disclosed.

In application EP 2 484 387 in the name of Q-Med, compositions based on hyaluronic acid and comprising a vitamin C derivative and also a local anesthetic are presented. In this application, the local anesthetic has an effect of limiting the degradation of certain rheological properties during autoclaving, while the vitamin C derivative has an opposite effect.

Local anesthetics are sometimes used in combination with polyols.

Hyaluronic acid-based compositions comprising both mannitol and lidocaine are sold; this is, for example, the case with the Stylage® products sold by Vivacy.

Application WO 2005/067994 in the name of Anika Therapeutics describes hyaluronic acid-based gels which comprise in particular lidocaine. Example 21 discloses that, on the compositions tested, lidocaine can have an effect limiting the degradation of some rheological properties during sterilization by moist heat (compared with the same sterilized composition not comprising lidocaine).

In application WO 2010/015901 in the name of Allergan, and in particular in example 4, lidocaine is added to a certain number of compositions based on crosslinked hyaluronic acid. Whatever the hyaluronic acid composition, the addition of lidocaine does not have the effect of improving rheological properties during heat sterilization, but does not however have an effect of degradation of said rheological properties.

Application WO 2010/052430 in the name of Anteis describes a hyaluronic acid-based composition comprising a glycerol/sorbitol mixture and also lidocaine. According to this application, the addition of lidocaine to compositions already comprising a glycerol/sorbitol mixture has the effect of limiting the degradation of the rheological properties of the compositions during autoclaving.

In conclusion, the prior art discloses that the addition of exemplified polyol(s) has the effect of limiting the degradation of the rheological properties of a hyaluronic acid-based composition during heat sterilization. Moreover, the antioxidant properties of polyols allow better persistence in vivo, and these properties confer a certain number of advantages on the compositions.

On the other hand, as regards lidocaine, the prior art discloses contradictory effects, the consequence of adding lidocaine being either to limit the degradation, or to cause degradation of the rheological properties, or to have few effects during heat sterilization.

As explained in the prior art, the addition of polyols is beneficial in vivo. In particular, their antioxidant and free-radical-scavenging effects are particularly beneficial, in particular for cells and DNA sequences. In addition, they improve the persistence of gels in vivo, and there is therefore a need for compositions comprising polyols.

Generally, the limitation of the degradation of some rheological properties brought about by the addition of a polyol is known from the prior art, but can present a drawback for hyaluronic acid-based compositions intended to be injected, since their viscosity and/or their viscoelastic properties may no longer be appropriate for the specifications of the injectable products. In particular, injection difficulties can arise and the rheological properties can be too different compared with those of the surrounding tissues.

As regards to the adaptation of the rheological properties with respect to those of the surrounding tissues, this makes it possible to limit the inflammatory phenomena and the feelings of discomfort and of the presence of a foreign body.

There is therefore a need to obtain hyaluronic acid-based compositions which have all the properties associated with the addition of at least one polyol, while at the same time making it possible to adapt their rheological properties to the specifications of injectable products, during heat sterilization, in particular moist heat sterilization.

Surprisingly, the applicant has shown that the incorporation of at least one local anesthetic, chosen from the group consisting of benzocaine, chloroprocaine, procaine, etidocaine, aptocaine, chlorobutanol, diamocaine, dyclonine, guafecainol, polidocanol, mepivacaine, prilocaine, articaine, bupivacaine, ropivacaine, tetracaine and salts thereof and isolated isomers thereof, to a sterilized aqueous composition based on hyaluronic acid already comprising at least one polyol has the effect of enabling the adaptation of the rheological properties of the composition during sterilization, i.e. a reduction in the elastic modulus G', in the viscous modulus G" and/or in the viscosity q.

This is particularly advantageous in the field of hyaluronic acid-based injectable compositions. Indeed, this makes it possible to obtain compositions in which the rheological properties are close to those of the surrounding tissues.

This is particularly advantageous in the field of hyaluronic acid-based injectable compositions. Indeed, this makes it possible to obtain compositions in which the rheology under low stress or at rest can be adapted to that of the surrounding tissues, which are resistant in vivo (by virtue in particular of the polyol(s)), and which do not cause any significant pain during injection (presence of at least one local anesthetic), which is a particularly appreciated and desired additional effect.

Finally, when the compositions according to the invention are confronted with high shear rates, found, for example:
during injection;
during friction of the skin once the composition has been injected (having a wash, facial expressions, etc.);
they behave in a manner similar to the same compositions not comprising the at least one local anesthetic, which is also surprising. Thus, the injectability is similar, and for example the facial expressions remain the same as with a composition not comprising the at least one local anesthetic.

The term "hyaluronic acid" refers to crosslinked or non-crosslinked hyaluronic acid, alone or as a mixture, optionally chemically modified by substitution, alone or as a mixture, optionally in the form of a salt thereof, alone or as a mixture.

The term "local anesthetic" refers to a local anesthetic or a salt thereof, alone or as a mixture.

Generally in the text of this application, the limits of a range of values are included in this range, in particular in the expression "between . . . and . . . ".

The term "Mw" or "molecular weight" refers to the weight-average molecular weight of the polymers, measured in Daltons.

In the present invention, the degree of crosslinking X is defined as being equal to the ratio:

$$X = \frac{\text{(Number of moles of crosslinking agent introduced into the reaction medium)}}{\text{(Number of moles of disaccharide unit introduced into the reaction medium)}}$$

The term "equivalent amount" refers to an amount equivalent in terms of weight, or of moles or equivalent bioavailability.

The term "rheological properties" refers to the elastic modulus (G'), the viscous modulus (G") and/or the dynamic viscosity (q).

The expression "degradation of the rheological properties during heat sterilization" refers to the reduction in value of the characteristic measured, compared with a composition not comprising the at least one polyol and/or the at least one local anesthetic. The principle characteristics measured are the elastic modulus (G'), the viscosity modulus (G") and/or the dynamic viscosity (q). When it is a question of the elastic modulus (G'), the value which decreases is that which is expressed in Pa·s. When it is a question of the dynamic viscosity (q), the value which decreases is that which is expressed in Pa·s. When it is a question of the viscous modulus (G"), the value which decreases is that which is expressed in Pa·s.

The term "injectability" refers to the ability of an injectable composition to be injected. Most commonly, the injectability is expressed in Newtons (N) for injecting with a 27G1/2 needle with a plunger speed of 13 mm/minute. Good injectability results in a low force (N) and, conversely, the greater the force (N), the more difficult the injectability is. The injectability can also be referred to as "extrusion force".

The invention relates to an injectable sterilized aqueous composition comprising at least one hyaluronic acid, at least one polyol and at least one local anesthetic chosen from the group consisting of benzocaine, chloroprocaine, procaine, etidocaine, aptocaine, chlorobutanol, diamocaine, dyclonine, guafecainol, polidocanol, mepivacaine, prilocaine, articaine, bupivacaine, ropivacaine, tetracaine and salts thereof and isolated isomers thereof.

In one embodiment, the injectable sterilized aqueous composition according to the invention is characterized in that the at least one local anesthetic is chosen from the group consisting of benzocaine, chloroprocaine, procaine, etidocaine, aptocaine, diamocaine, dyclonine, guafecainol, mepivacaine, prilocaine, articaine, bupivacaine, ropivacaine, tetracaine and salts thereof and isolated isomers thereof.

In one embodiment, the injectable sterilized aqueous composition according to the invention is characterized in that the at least one local anesthetic is chosen from the group consisting of benzocaine, chloroprocaine, procaine, etidocaine, aptocaine, diamocaine, mepivacaine, prilocaine, articaine, bupivacaine, ropivacaine, tetracaine and salts thereof and isolated isomers thereof.

In one embodiment, the injectable sterilized aqueous composition according to the invention is characterized in that the at least one local anesthetic is chosen from the group consisting of benzocaine, chloroprocaine, procaine, etidocaine and salts thereof.

In one embodiment, the injectable sterilized aqueous composition according to the invention is characterized in that the at least one local anesthetic is benzocaine.

In one embodiment, the injectable sterilized aqueous composition according to the invention is characterized in that the at least one local anesthetic is chloroprocaine.

In one embodiment, the injectable sterilized aqueous composition according to the invention is characterized in that the at least one local anesthetic is procaine.

In one embodiment, the injectable sterilized aqueous composition according to the invention is characterized in that the at least one local anesthetic is etidocaine.

In one embodiment, the injectable sterilized aqueous composition according to the invention is characterized in that the at least one local anesthetic is chosen from the group consisting of aptocaine, chlorobutanol, diamocaine, dyclonine, guafecainol, polidocanol, and salts thereof and isolated isomers thereof.

In one embodiment, the injectable sterilized aqueous composition according to the invention is characterized in that the at least one local anesthetic is aptocaine.

In one embodiment, the injectable sterilized aqueous composition according to the invention is characterized in that the at least one local anesthetic is chlorobutanol.

In one embodiment, the injectable sterilized aqueous composition according to the invention is characterized in that the at least one local anesthetic is diamocaine.

In one embodiment, the injectable sterilized aqueous composition according to the invention is characterized in that the at least one local anesthetic is dyclonine.

In one embodiment, the injectable sterilized aqueous composition according to the invention is characterized in that the at least one local anesthetic is guafecainol.

In one embodiment, the injectable sterilized aqueous composition according to the invention is characterized in that the at least one local anesthetic is polidocanol.

In one embodiment, the injectable sterilized aqueous composition according to the invention is characterized in that the at least one local anesthetic is chosen from the group consisting of mepivacaine, prilocaine and salts thereof and isolated isomers thereof.

In one embodiment, the injectable sterilized aqueous composition according to the invention is characterized in that the at least one local anesthetic is mepivacaine.

In one embodiment, the injectable sterilized aqueous composition according to the invention is characterized in that the at least one local anesthetic is prilocaine.

In one embodiment, the injectable sterilized aqueous composition according to the invention is characterized in that the at least one local anesthetic is chosen from the group consisting of articaine, bupivacaine, ropivacaine, tetracaine and salts thereof and isolated isomers thereof.

In one embodiment, the injectable sterilized aqueous composition according to the invention is characterized in that the at least one local anesthetic is articaine.

In one embodiment, the injectable sterilized aqueous composition according to the invention is characterized in that the at least one local anesthetic is bupivacaine.

In one embodiment, the injectable sterilized aqueous composition according to the invention is characterized in that the at least one local anesthetic is ropivacaine.

In one embodiment, the injectable sterilized aqueous composition according to the invention is characterized in that the at least one local anesthetic is tetracaine.

In one embodiment, the injectable sterilized aqueous composition according to the invention comprises at least one non-crosslinked hyaluronic acid or a salt thereof, alone or as a mixture.

In one embodiment, the injectable sterilized aqueous composition according to the invention comprises at least one crosslinked hyaluronic acid or a salt thereof, alone or as a mixture.

In one embodiment, the injectable sterilized aqueous composition according to the invention is characterized in that the at least one crosslinked hyaluronic acid has a degree of crosslinking X of between 0.001 and 0.5.

In one embodiment, the injectable sterilized aqueous composition according to the invention is characterized in that the at least one crosslinked hyaluronic acid has a degree of crosslinking X of between 0.01 and 0.4.

In one embodiment, the injectable sterilized aqueous composition according to the invention is characterized in that the at least one crosslinked hyaluronic acid has a degree of crosslinking X of between 0.1 and 0.3.

In one embodiment, the injectable sterilized aqueous composition according to the invention is characterized in that the at least one crosslinked hyaluronic acid has a degree of crosslinking X of 0.06.

In one embodiment, the injectable sterilized aqueous composition according to the invention is characterized in that the at least one crosslinked hyaluronic acid has a degree of crosslinking X of 0.07.

In one embodiment, the injectable sterilized aqueous composition according to the invention is characterized in that the at least one crosslinked hyaluronic acid has a degree of crosslinking X of 0.12.

In one embodiment, the composition according to the invention is characterized in that the molecular weight Mw of the at least one hyaluronic acid is in a range between 0.01 MDa and 5 MDa.

In one embodiment, the composition according to the invention is characterized in that the molecular weight Mw of the at least one hyaluronic acid is in a range between 0.1 MDa and 3.5 MDa.

In one embodiment, the composition according to the invention is characterized in that the molecular weight Mw of the at least one hyaluronic acid is in a range between 1 MDa and 3 MDa.

In one embodiment, the composition according to the invention is characterized in that the molecular weight Mw of the at least one hyaluronic acid is in a range between 1 MDa and 2 MDa.

In one embodiment, the composition according to the invention is characterized in that the molecular weight Mw of the at least one hyaluronic acid is 1 MDa.

In one embodiment, the composition according to the invention is characterized in that the molecular weight Mw of the at least one hyaluronic acid is 2 MDa.

In one embodiment, the composition according to the invention is characterized in that the molecular weight Mw of the at least one hyaluronic acid is 3 MDa.

In one embodiment, the injectable sterilized aqueous composition according to the invention comprises at least one crosslinked or non-crosslinked hyaluronic acid chemically modified by substitution, or a salt thereof, alone or as a mixture.

In one embodiment, the injectable sterilized aqueous composition according to the invention comprises at least one doubly crosslinked hyaluronic acid as described in patent application WO 2000/046253 in the name of Fermentech Medical Limited.

In one embodiment, the injectable sterilized aqueous composition according to the invention comprises a mixture of crosslinked or non-crosslinked hyaluronic acids or a salt thereof.

In one embodiment, the injectable sterilized aqueous composition according to the invention comprises a mixture of crosslinked hyaluronic acids or a salt thereof.

In one embodiment, the mixture of crosslinked hyaluronic acids or a salt thereof is a single-phase mixture such as the one described in patent application WO 2009/071697 in the name of the applicant.

In one embodiment, the mixture of crosslinked hyaluronic acids or a salt thereof is a mixture obtained by mixing several hyaluronic acids, or a salt thereof, of different molecular weights prior to their crosslinking, as described in patent application WO 2004/092222 in the name of Corneal Industrie.

In one embodiment, the injectable sterilized aqueous composition according to the invention comprises at least one hyaluronic acid, or a salt thereof, substituted with a group providing lipophilic or hydrating properties, for instance the substituted hyaluronic acids as described in patent application FR 2 983 483 in the name of the applicant.

In one embodiment, the injectable sterilized aqueous composition according to the invention is characterized in that at least one hyaluronic acid is in the form of a sodium salt or of a potassium salt.

In one embodiment, the injectable sterilized aqueous composition according to the invention comprises at least one co-crosslinked hyaluronic acid or a salt thereof, alone or as a mixture.

In one embodiment, the injectable sterilized aqueous composition according to the invention is characterized in that the concentration of the at least one hyaluronic acid [HA] is between 2 mg/g and 50 mg/g of total weight of said composition.

In one embodiment, the injectable sterilized aqueous composition according to the invention is characterized in that the concentration of the at least one hyaluronic acid [HA] is between 4 mg/g and 40 mg/g of total weight of said composition.

In one embodiment, the injectable sterilized aqueous composition according to the invention is characterized in that the concentration of the at least one hyaluronic acid [HA] is between 5 mg/g and 30 mg/g of total weight of said composition.

In one embodiment, the injectable sterilized aqueous composition according to the invention is characterized in that the concentration of the at least one hyaluronic acid [HA] is between 10 mg/g and 30 mg/g of total weight of said composition.

In one embodiment, the injectable sterilized aqueous composition according to the invention is characterized in that the concentration of the at least one hyaluronic acid [HA] is 20 mg/g of total weight of said composition.

In one embodiment, the injectable sterilized aqueous composition according to the invention is characterized in that the concentration of the at least one hyaluronic acid is between 0.2% and 5% by weight relative to the total weight of said composition.

In one embodiment, the injectable sterilized aqueous composition according to the invention is characterized in that the concentration of the at least one hyaluronic acid is greater than or equal to 1% by weight relative to the total weight of said composition.

In one embodiment, the injectable sterilized aqueous composition according to the invention is characterized in that the at least one polyol is chosen from the group consisting of glycerol, sorbitol, propylene glycol, xylitol, mannitol, erythritol, maltitol and lactitol, alone or as mixture.

In one embodiment, the injectable sterilized aqueous composition according to the invention is characterized in that the at least one polyol is chosen from the group consisting of mannitol, sorbitol, maltitol and glycerol, alone or as a mixture.

In one embodiment, the injectable sterilized aqueous composition according to the invention is characterized in that the at least one polyol is chosen from the group consisting of mannitol, sorbitol and maltitol, alone or as a mixture.

In one embodiment, the injectable sterilized aqueous composition according to the invention is characterized in that the at least one polyol is mannitol.

In one embodiment, the injectable sterilized aqueous composition according to the invention is characterized in that the at least one polyol is sorbitol.

In one embodiment, the injectable sterilized aqueous composition according to the invention is characterized in that the at least one polyol is maltitol.

In one embodiment, the injectable sterilized aqueous composition according to the invention is characterized in that the at least one polyol is glycerol.

In one embodiment, the injectable sterilized aqueous composition according to the invention comprises at least mannitol and sorbitol.

In one embodiment, the injectable sterilized aqueous composition according to the invention comprises at least mannitol and maltitol.

In one embodiment, the injectable sterilized aqueous composition according to the invention is characterized in that the concentration of the at least one polyol [Po] is between 0.01 mg/g and 50 mg/g.

In one embodiment, the injectable sterilized aqueous composition according to the invention is characterized in that the concentration of the at least one polyol [Po] is between 10 and 40 mg/g of total weight of said composition.

In one embodiment, the injectable sterilized aqueous composition according to the invention is characterized in that the concentration of the at least one polyol [Po] is between 15 and 30 mg/g of total weight of said composition.

In one embodiment, the injectable sterilized aqueous composition according to the invention is characterized in that the concentration of the at least one polyol [Po] is between 15 and 25 mg/g of total weight of said composition.

In one embodiment, the injectable sterilized aqueous composition according to the invention is characterized in that the concentration of the at least one polyol [Po] is between 20 and 40 mg/g of total weight of said composition.

In one embodiment, the injectable sterilized aqueous composition according to the invention is characterized in that the concentration of the at least one polyol [Po] is between 20 and 30 mg/g of total weight of said composition.

In one embodiment, the injectable sterilized aqueous composition according to the invention is characterized in that the concentration of the at least one polyol [Po] is between 25 and 35 mg/g of total weight of said composition.

In one embodiment, the injectable sterilized aqueous composition according to the invention is characterized in that the concentration of the at least one polyol [Po] is 35 mg/g of total weight of said composition.

In one embodiment, the injectable sterilized aqueous composition according to the invention is characterized in that the at least one polyol is mannitol and the concentration thereof is between 10 and 40 mg/g of total weight of said composition.

In one embodiment, the injectable sterilized aqueous composition according to the invention is characterized in that the at least one polyol is mannitol and the concentration thereof is between 15 and 30 mg/g of total weight of said composition.

In one embodiment, the injectable sterilized aqueous composition according to the invention is characterized in that the at least one polyol is mannitol and the concentration thereof is between 15 and 25 mg/g of total weight of said composition.

In one embodiment, the injectable sterilized aqueous composition according to the invention is characterized in that the at least one polyol is mannitol and the concentration thereof is between 20 and 40 mg/g of total weight of said composition.

In one embodiment, the injectable sterilized aqueous composition according to the invention is characterized in that the at least one polyol is mannitol and the concentration thereof is between 25 and 35 mg/g of total weight of said composition.

In one embodiment, the injectable sterilized aqueous composition according to the invention is characterized in that the at least one polyol is mannitol and the concentration thereof is 35 mg/g of total weight of said composition.

In one embodiment, the injectable sterilized aqueous composition according to the invention is characterized in that the at least one polyol is sorbitol and the concentration thereof is between 10 and 40 mg/g of total weight of said composition.

In one embodiment, the injectable sterilized aqueous composition according to the invention is characterized in that the at least one polyol is sorbitol and the concentration thereof is between 15 and 30 mg/g of total weight of said composition.

In one embodiment, the injectable sterilized aqueous composition according to the invention is characterized in that the at least one polyol is sorbitol and the concentration thereof is between 15 and 25 mg/g of total weight of said composition.

In one embodiment, the injectable sterilized aqueous composition according to the invention is characterized in that the at least one polyol is sorbitol and the concentration thereof is between 20 and 40 mg/g of total weight of said composition.

In one embodiment, the injectable sterilized aqueous composition according to the invention is characterized in that the at least one polyol is sorbitol and the concentration thereof is between 25 and 35 mg/g of total weight of said composition.

In one embodiment, the injectable sterilized aqueous composition according to the invention is characterized in that the at least one polyol is sorbitol and the concentration thereof is 35 mg/g of total weight of said composition.

In one embodiment, the injectable sterilized aqueous composition according to the invention is characterized in that the at least one polyol is maltitol and the concentration thereof is between 10 and 40 mg/g of total weight of said composition.

In one embodiment, the injectable sterilized aqueous composition according to the invention is characterized in that the at least one polyol is maltitol and the concentration thereof is between 15 and 30 mg/g of total weight of said composition.

In one embodiment, the injectable sterilized aqueous composition according to the invention is characterized in that the at least one polyol is maltitol and the concentration thereof is between 15 and 25 mg/g of total weight of said composition.

In one embodiment, the injectable sterilized aqueous composition according to the invention is characterized in that the at least one polyol is maltitol and the concentration thereof is between 20 and 40 mg/g of total weight of said composition.

In one embodiment, the injectable sterilized aqueous composition according to the invention is characterized in that the at least one polyol is maltitol and the concentration thereof is between 25 and 35 mg/g of total weight of said composition.

In one embodiment, the injectable sterilized aqueous composition according to the invention is characterized in that the at least one polyol is maltitol and the concentration thereof is 35 mg/g of total weight of said composition.

In one embodiment, the injectable sterilized aqueous composition according to the invention is characterized in that the at least one polyol is glycerol and the concentration thereof is between 10 and 40 mg/g of total weight of said composition.

In one embodiment, the injectable sterilized aqueous composition according to the invention is characterized in that the at least one polyol is glycerol and the concentration thereof is between 15 and 30 mg/g of total weight of said composition.

In one embodiment, the injectable sterilized aqueous composition according to the invention is characterized in that the at least one polyol is glycerol and the concentration thereof is between 15 and 25 mg/g of total weight of said composition.

In one embodiment, the injectable sterilized aqueous composition according to the invention is characterized in that the at least one polyol is glycerol and the concentration thereof is between 20 and 40 mg/g of total weight of said composition.

In one embodiment, the injectable sterilized aqueous composition according to the invention is characterized in that the at least one polyol is glycerol and the concentration thereof is between 25 and 35 mg/g of total weight of said composition.

In one embodiment, the injectable sterilized aqueous composition according to the invention is characterized in that the at least one polyol is glycerol and the concentration thereof is 35 mg/g of total weight of said composition.

In one embodiment, the injectable sterilized aqueous composition according to the invention is characterized in that the concentration of the at least one local anesthetic [AL] is between 0.01 mg/g and 50 mg/g of total weight of said composition.

In one embodiment, the injectable sterilized aqueous composition according to the invention is characterized in that the concentration of the at least one local anesthetic [AL] is between 0.05 mg/g and 45 mg/g of total weight of said composition.

In one embodiment, the injectable sterilized aqueous composition according to the invention is characterized in that the concentration of the at least one local anesthetic [AL] is between 0.1 mg/g and 40 mg/g of total weight of said composition.

In one embodiment, the injectable sterilized aqueous composition according to the invention is characterized in that the concentration of the at least one local anesthetic [AL] is between 0.2 mg/g and 30 mg/g of total weight of said composition.

In one embodiment, the injectable sterilized aqueous composition according to the invention is characterized in that the concentration of the at least one local anesthetic [AL] is between 0.5 mg/g and 20 mg/g of total weight of said composition.

In one embodiment, the injectable sterilized aqueous composition according to the invention is characterized in that the concentration of the at least one local anesthetic [AL] is between 1 mg/g and 15 mg/g of total weight of said composition.

In one embodiment, the injectable sterilized aqueous composition according to the invention is characterized in that the concentration of the at least one local anesthetic [AL] is between 1 mg/g and 10 mg/g of total weight of said composition.

In one embodiment, the injectable sterilized aqueous composition according to the invention is characterized in that the concentration of the at least one local anesthetic [AL] is between 1 mg/g and 6 mg/g of total weight of said composition.

In one embodiment, the injectable sterilized aqueous composition according to the invention is characterized in that the concentration of the at least one local anesthetic [AL] is between 1 mg/g and 5 mg/g of total weight of said composition.

In one embodiment, the injectable sterilized aqueous composition according to the invention is characterized in that the concentration of the at least one local anesthetic [AL] is between 2 mg/g and 5 mg/g of total weight of said composition.

In one embodiment, the injectable sterilized aqueous composition according to the invention is characterized in that the concentration of the at least one local anesthetic [AL] is between 6 mg/g and 10 mg/g of total weight of said composition.

In one embodiment, the injectable sterilized aqueous composition according to the invention is characterized in that the concentration of the at least one local anesthetic [AL] is 1 mg/g of total weight of said composition.

In one embodiment, the injectable sterilized aqueous composition according to the invention is characterized in that the concentration of the at least one local anesthetic [AL] is 3 mg/g of total weight of said composition.

In one embodiment, the injectable sterilized aqueous composition according to the invention is characterized in that the concentration of the at least one local anesthetic [AL] is 4 mg/g of total weight of said composition.

In one embodiment, the injectable sterilized aqueous composition according to the invention is characterized in that the concentration of the at least one local anesthetic [AL] is 5 mg/g of total weight of said composition.

In one embodiment, the injectable sterilized aqueous composition according to the invention is characterized in that the concentration of the at least one local anesthetic [AL] is 6 mg/g of total weight of said composition.

In one embodiment, the injectable sterilized aqueous composition according to the invention is characterized in that the concentration of the at least one local anesthetic [AL] is 10 mg/g of total weight of said composition.

In one embodiment, the injectable sterilized aqueous composition according to the invention is characterized in that the at least one local anesthetic is benzocaine [BENZ], and wherein the concentration of benzocaine [BENZ] is between 0.01 mg/g and 50 mg/g of total weight of said composition.

In one embodiment, the injectable sterilized aqueous composition according to the invention is characterized in that the at least one local anesthetic is benzocaine [BENZ], and wherein the concentration of benzocaine [BENZ] is between 1 mg/g and 15 mg/g of total weight of said composition.

In one embodiment, the injectable sterilized aqueous composition according to the invention is characterized in that the at least one local anesthetic is benzocaine [BENZ], and wherein the concentration of benzocaine [BENZ] is between 1 mg/g and 6 mg/g of total weight of said composition.

In one embodiment, the injectable sterilized aqueous composition according to the invention is characterized in that the at least one local anesthetic is benzocaine [BENZ], and wherein the concentration of benzocaine [BENZ] is approximately 3 mg/g of total weight of said composition.

In one embodiment, the injectable sterilized aqueous composition according to the invention is characterized in that the at least one local anesthetic is chloroprocaine [CHPR], and wherein the concentration of chloroprocaine [CHPR] is between 0.01 mg/g and 50 mg/g of total weight of said composition.

In one embodiment, the injectable sterilized aqueous composition according to the invention is characterized in that the at least one local anesthetic is chloroprocaine [CHPR], and wherein the concentration of chloroprocaine [CHPR] is between 1 mg/g and 15 mg/g of total weight of said composition.

In one embodiment, the injectable sterilized aqueous composition according to the invention is characterized in that the at least one local anesthetic is chloroprocaine [CHPR], and wherein the concentration of chloroprocaine [CHPR] is between 1 mg/g and 6 mg/g of total weight of said composition.

In one embodiment, the injectable sterilized aqueous composition according to the invention is characterized in that the at least one local anesthetic is chloroprocaine [CHPR], and wherein the concentration of chloroprocaine [CHPR] is approximately 3 mg/g of total weight of said composition.

In one embodiment, the injectable sterilized aqueous composition according to the invention is characterized in that the at least one local anesthetic is procaine [PROC], and wherein the concentration of procaine [PROC] is between 0.01 mg/g and 50 mg/g of total weight of said composition.

In one embodiment, the injectable sterilized aqueous composition according to the invention is characterized in that the at least one local anesthetic is procaine [PROC], and wherein the concentration of procaine [PROC] is between 1 mg/g and 15 mg/g of total weight of said composition.

In one embodiment, the injectable sterilized aqueous composition according to the invention is characterized in that the at least one local anesthetic is procaine [PROC], and wherein the concentration of procaine [PROC] is between 1 mg/g and 6 mg/g of total weight of said composition.

In one embodiment, the injectable sterilized aqueous composition according to the invention is characterized in that the at least one local anesthetic is procaine [PROC], and wherein the concentration of procaine [PROC] is approximately 3 mg/g of total weight of said composition.

In one embodiment, the injectable sterilized aqueous composition according to the invention is characterized in that the at least one local anesthetic is etidocaine [ETID], and wherein the concentration of etidocaine [ETID] is between 0.01 mg/g and 50 mg/g of total weight of said composition.

In one embodiment, the injectable sterilized aqueous composition according to the invention is characterized in that the at least one local anesthetic is etidocaine [ETID], and wherein the concentration of etidocaine [ETID] is between 1 mg/g and 15 mg/g of total weight of said composition.

In one embodiment, the injectable sterilized aqueous composition according to the invention is characterized in that the at least one local anesthetic is etidocaine [ETID], and wherein the concentration of etidocaine [ETID] is between 1 mg/g and 6 mg/g of total weight of said composition.

In one embodiment, the injectable sterilized aqueous composition according to the invention is characterized in that the at least one local anesthetic is etidocaine [ETID], and wherein the concentration of etidocaine [ETID] is approximately 3 mg/g of total weight of said composition.

In one embodiment, the injectable sterilized aqueous composition according to the invention is characterized in that the at least one local anesthetic is aptocaine [APTO], and wherein the concentration of aptocaine [APTO] is between 0.01 mg/g and 50 mg/g of total weight of said composition.

In one embodiment, the injectable sterilized aqueous composition according to the invention is characterized in that the at least one local anesthetic is aptocaine [APTO], and wherein the concentration of aptocaine [APTO] is between 1 mg/g and 15 mg/g of total weight of said composition.

In one embodiment, the injectable sterilized aqueous composition according to the invention is characterized in that the at least one local anesthetic is aptocaine [APTO], and wherein the concentration of aptocaine [APTO] is between 1 mg/g and 6 mg/g of total weight of said composition.

In one embodiment, the injectable sterilized aqueous composition according to the invention is characterized in that the at least one local anesthetic is aptocaine [APTO], and wherein the concentration of aptocaine [APTO] is approximately 3 mg/g of total weight of said composition.

In one embodiment, the injectable sterilized aqueous composition according to the invention is characterized in that the at least one local anesthetic is chlorobutanol [CHLO], and wherein the concentration of chlorobutanol [CHLO] is between 0.01 mg/g and 50 mg/g of total weight of said composition.

In one embodiment, the injectable sterilized aqueous composition according to the invention is characterized in that the at least one local anesthetic is chlorobutanol [CHLO], and wherein the concentration of chlorobutanol [CHLO] is between 1 mg/g and 15 mg/g of total weight of said composition.

In one embodiment, the injectable sterilized aqueous composition according to the invention is characterized in that the at least one local anesthetic is chlorobutanol [CHLO], and wherein the concentration of chlorobutanol [CHLO] is between 1 mg/g and 6 mg/g of total weight of said composition.

In one embodiment, the injectable sterilized aqueous composition according to the invention is characterized in that the at least one local anesthetic is chlorobutanol [CHLO], and wherein the concentration of chlorobutanol [CHLO] is approximately 3 mg/g of total weight of said composition.

In one embodiment, the injectable sterilized aqueous composition according to the invention is characterized in that the at least one local anesthetic is diamocaine [DIAM], and wherein the concentration of diamocaine [DIAM] is between 0.01 mg/g and 50 mg/g of total weight of said composition.

In one embodiment, the injectable sterilized aqueous composition according to the invention is characterized in that the at least one local anesthetic is diamocaine [DIAM], and wherein the concentration of diamocaine [DIAM] is between 1 mg/g and 15 mg/g of total weight of said composition.

In one embodiment, the injectable sterilized aqueous composition according to the invention is characterized in that the at least one local anesthetic is diamocaine [DIAM], and wherein the concentration of diamocaine [DIAM] is between 1 mg/g and 6 mg/g of total weight of said composition.

In one embodiment, the injectable sterilized aqueous composition according to the invention is characterized in that the at least one local anesthetic is diamocaine [DIAM], and wherein the concentration of diamocaine [DIAM] is approximately 3 mg/g of total weight of said composition.

In one embodiment, the injectable sterilized aqueous composition according to the invention is characterized in that the at least one local anesthetic is dyclonine [DYCL], and wherein the concentration of dyclonine [DYCL] is between 0.01 mg/g and 50 mg/g of total weight of said composition.

In one embodiment, the injectable sterilized aqueous composition according to the invention is characterized in that the at least one local anesthetic is dyclonine [DYCL], and wherein the concentration of dyclonine [DYCL] is between 1 mg/g and 15 mg/g of total weight of said composition.

In one embodiment, the injectable sterilized aqueous composition according to the invention is characterized in that the at least one local anesthetic is dyclonine [DYCL], and wherein the concentration of dyclonine [DYCL] is between 1 mg/g and 6 mg/g of total weight of said composition.

In one embodiment, the injectable sterilized aqueous composition according to the invention is characterized in that the at least one local anesthetic is dyclonine [DYCL], and wherein the concentration of dyclonine [DYCL] is approximately 3 mg/g of total weight of said composition.

In one embodiment, the injectable sterilized aqueous composition according to the invention is characterized in that the at least one local anesthetic is guafecainol [GUAF], and wherein the concentration of guafecainol [GUAF] is between 0.01 mg/g and 50 mg/g of total weight of said composition.

In one embodiment, the injectable sterilized aqueous composition according to the invention is characterized in that the at least one local anesthetic is guafecainol [GUAF], and wherein the concentration of guafecainol [GUAF] is between 1 mg/g and 15 mg/g of total weight of said composition.

In one embodiment, the injectable sterilized aqueous composition according to the invention is characterized in that the at least one local anesthetic is guafecainol [GUAF], and wherein the concentration of guafecainol [GUAF] is between 1 mg/g and 6 mg/g of total weight of said composition.

In one embodiment, the injectable sterilized aqueous composition according to the invention is characterized in that the at least one local anesthetic is guafecainol [GUAF], and wherein the concentration of guafecainol [GUAF] is approximately 3 mg/g of total weight of said composition.

In one embodiment, the injectable sterilized aqueous composition according to the invention is characterized in that the at least one local anesthetic is polidocanol [POLI], and wherein the concentration of polidocanol [POLI] is between 0.01 mg/g and 50 mg/g of total weight of said composition.

In one embodiment, the injectable sterilized aqueous composition according to the invention is characterized in that the at least one local anesthetic is polidocanol [POLI], and wherein the concentration of polidocanol [POLI] is between 1 mg/g and 15 mg/g of total weight of said composition.

In one embodiment, the injectable sterilized aqueous composition according to the invention is characterized in that the at least one local anesthetic is polidocanol [POLI], and wherein the concentration of polidocanol [POLI] is between 1 mg/g and 6 mg/g of total weight of said composition.

In one embodiment, the injectable sterilized aqueous composition according to the invention is characterized in that the at least one local anesthetic is polidocanol [POLI], and wherein the concentration of polidocanol [POLI] is approximately 3 mg/g of total weight of said composition.

In one embodiment, the injectable sterilized aqueous composition according to the invention is characterized in that the at least one local anesthetic is mepivacaine [MEPI], and wherein the concentration of mepicavaine [MEPI] is between 0.01 mg/g and 50 mg/g of total weight of said composition.

In one embodiment, the injectable sterilized aqueous composition according to the invention is characterized in that the at least one local anesthetic is mepivacaine [MEPI], and wherein the concentration of mepicavaine [MEPI] is between 1 mg/g and 15 mg/g of total weight of said composition.

In one embodiment, the injectable sterilized aqueous composition according to the invention is characterized in that the at least one local anesthetic is mepivacaine [MEPI], and wherein the concentration of mepicavaine [MEPI] is between 1 mg/g and 6 mg/g of total weight of said composition.

In one embodiment, the injectable sterilized aqueous composition according to the invention is characterized in that the at least one local anesthetic is mepivacaine [MEPI], and wherein the concentration of mepicavaine [MEPI] is approximately 3 mg/g of total weight of said composition.

In one embodiment, the injectable sterilized aqueous composition according to the invention is characterized in that the at least one local anesthetic is prilocaine [PRILO], and wherein the concentration of prilocaine [PRILO] is between 0.01 mg/g and 50 mg/g of total weight of said composition.

In one embodiment, the injectable sterilized aqueous composition according to the invention is characterized in that the at least one local anesthetic is prilocaine [PRILO], and wherein the concentration of prilocaine [PRILO] is between 1 mg/g and 15 mg/g of total weight of said composition.

In one embodiment, the injectable sterilized aqueous composition according to the invention is characterized in that the at least one local anesthetic is prilocaine [PRILO], and wherein the concentration of prilocaine [PRILO] is between 1 mg/g and 6 mg/g of total weight of said composition.

In one embodiment, the injectable sterilized aqueous composition according to the invention is characterized in that the at least one local anesthetic is prilocaine [PRILO], and wherein the concentration of prilocaine [PRILO] is approximately 3 mg/g of total weight of said composition.

In one embodiment, the injectable sterilized aqueous composition according to the invention is characterized in that the at least one local anesthetic is articaine [ARTI], and wherein the concentration of articaine [ARTI] is between 0.01 mg/g and 50 mg/g of total weight of said composition.

In one embodiment, the injectable sterilized aqueous composition according to the invention is characterized in that the at least one local anesthetic is articaine [ARTI], and wherein the concentration of articaine [ARTI] is between 1 mg/g and 15 mg/g of total weight of said composition.

In one embodiment, the injectable sterilized aqueous composition according to the invention is characterized in that the at least one local anesthetic is articaine [ARTI], and wherein the concentration of articaine [ARTI] is between 1 mg/g and 6 mg/g of total weight of said composition.

In one embodiment, the injectable sterilized aqueous composition according to the invention is characterized in that the at least one local anesthetic is articaine [ARTI], and wherein the concentration of articaine [ARTI] is approximately 3 mg/g of total weight of said composition.

In one embodiment, the injectable sterilized aqueous composition according to the invention is characterized in that the at least one local anesthetic is bupivacaine [BUPI], and wherein the concentration of bupivacaine [BUPI] is between 0.01 mg/g and 50 mg/g of total weight of said composition.

In one embodiment, the injectable sterilized aqueous composition according to the invention is characterized in that the at least one local anesthetic is bupivacaine [BUPI], and wherein the concentration of bupivacaine [BUPI] is between 1 mg/g and 15 mg/g of total weight of said composition.

In one embodiment, the injectable sterilized aqueous composition according to the invention is characterized in that the at least one local anesthetic is bupivacaine [BUPI], and wherein the concentration of bupivacaine [BUPI] is between 1 mg/g and 6 mg/g of total weight of said composition.

In one embodiment, the injectable sterilized aqueous composition according to the invention is characterized in that the at least one local anesthetic is bupivacaine [BUPI], and wherein the concentration of bupivacaine [BUPI] is approximately 3 mg/g of total weight of said composition.

In one embodiment, the injectable sterilized aqueous composition according to the invention is characterized in that the at least one local anesthetic is ropivacaine [ROPI], and wherein the concentration of ropivacaine [ROPI] is between 0.01 mg/g and 50 mg/g of total weight of said composition.

In one embodiment, the injectable sterilized aqueous composition according to the invention is characterized in that the at least one local anesthetic is ropivacaine [ROPI], and wherein the concentration of ropivacaine [ROPI] is between 1 mg/g and 15 mg/g of total weight of said composition.

In one embodiment, the injectable sterilized aqueous composition according to the invention is characterized in that the at least one local anesthetic is ropivacaine [ROPI], and wherein the concentration of ropivacaine [ROPI] is between 1 mg/g and 6 mg/g of total weight of said composition.

In one embodiment, the injectable sterilized aqueous composition according to the invention is characterized in that the at least one local anesthetic is ropivacaine [ROPI], and wherein the concentration of ropivacaine [ROPI] is approximately 3 mg/g of total weight of said composition.

In one embodiment, the injectable sterilized aqueous composition according to the invention is characterized in that the at least one local anesthetic is tetracaine [TETRA], and wherein the concentration of tetracaine [TETRA] is between 0.01 mg/g and 50 mg/g of total weight of said composition.

In one embodiment, the injectable sterilized aqueous composition according to the invention is characterized in that the at least one local anesthetic is tetracaine [TETRA], and wherein the concentration of tetracaine [TETRA] is between 1 mg/g and 15 mg/g of total weight of said composition.

In one embodiment, the injectable sterilized aqueous composition according to the invention is characterized in that the at least one local anesthetic is tetracaine [TETRA], and wherein the concentration of tetracaine [TETRA] is between 1 mg/g and 6 mg/g of total weight of said composition.

In one embodiment, the injectable sterilized aqueous composition according to the invention is characterized in that the at least one local anesthetic is tetracaine [TETRA], and wherein the concentration of tetracaine [TETRA] is approximately 3 mg/g of total weight of said composition.

In one embodiment, the composition according to the invention is characterized in that the weight ratio between the concentration of the at least one polyol [Po] and the concentration of the at least one local anesthetic [AL]: [Po]/[AL] is between 0.0002 and 5000; $0.0002 \leq [Po]/[AL] \leq 5000$.

In one embodiment, the composition according to the invention is characterized in that the weight ratio between the concentration of the at least one polyol [Po] and the concentration of the at least one local anesthetic [AL]: [Po]/[AL] is between 0.002 and 500; $0.002 \leq [Po]/[AL] \leq 500$.

In one embodiment, the composition according to the invention is characterized in that the weight ratio between the concentration of the at least one polyol [Po] and the concentration of the at least one local anesthetic [AL]: [Po]/[AL] is between 0.02 and 50; $0.02 \leq [Po]/[AL] \leq 50$.

In one embodiment, the composition according to the invention is characterized in that the weight ratio between the concentration of the at least one polyol [Po] and the concentration of the at least one local anesthetic [AL]: [Po]/[AL] is between 1 and 20; $1 \leq [Po]/[AL] \leq 20$.

In one embodiment, the composition according to the invention is characterized in that the weight ratio between the concentration of the at least one polyol [Po] and the concentration of the at least one local anesthetic [AL]: [Po]/[AL] is between 3 and 15; $3 \leq [Po]/[AL] \leq 15$.

In one embodiment, the composition according to the invention is characterized in that the weight ratio between the concentration of the at least one polyol [Po] and the concentration of the at least one local anesthetic [AL]: [Po]/[AL] is between 4 and 8; $4 \leq [Po]/[AL] \leq 8$.

In one embodiment, the composition according to the invention is characterized in that the weight ratio between the concentration of the at least one polyol [Po] and the concentration of the at least one local anesthetic [AL]: [Po]/[AL] is between 10 and 13; $10 \leq [Po]/[AL] \leq 13$.

In one embodiment, the composition according to the invention is characterized in that the weight ratio between the concentration of the at least one hyaluronic acid [HA] and the concentration of the at least one local anesthetic [AL]: [HA]/[AL] is between 0.1 and 50; $0.1 \leq [HA]/[AL] \leq 50$.

In one embodiment, the injectable sterilized aqueous composition according to the invention is characterized in that the weight ratio between the concentration of the at least one hyaluronic acid [HA] and the concentration of the at least one local anesthetic [AL]: [HA]/[AL] is between 0.5 and 40; $0.5 \leq [HA]/[AL] \leq 40$.

In one embodiment, the injectable sterilized aqueous composition according to the invention is characterized in that the weight ratio between the concentration of the at least one hyaluronic acid [HA] and the concentration of the at least one local anesthetic [AL]: [HA]/[AL] is between 1 and 30; $1 \leq [HA]/[AL] \leq 30$.

In one embodiment, the injectable sterilized aqueous composition according to the invention is characterized in that the weight ratio between the concentration of the at least one hyaluronic acid [HA] and the concentration of the at least one local anesthetic [AL]: [HA]/[AL] is between 2 and 20; $2 \leq [HA]/[AL] \leq 20$.

In one embodiment, the injectable sterilized aqueous composition according to the invention is characterized in that the weight ratio between the concentration of the at least one hyaluronic acid [HA] and the concentration of the at least one local anesthetic [AL]: [HA]/[AL] is between 7/3 and 26/3; $7/3 \leq [HA]/[AL] \leq 26/3$.

In one embodiment, the injectable sterilized aqueous composition according to the invention is characterized in that the weight ratio between the concentration of the at least one hyaluronic acid [HA] and the concentration of the at least one local anesthetic [AL]: [HA]/[AL] is between 2 and 20/3; $2 \leq [HA]/[AL] \leq 20/3$.

In one embodiment, the injectable sterilized aqueous composition according to the invention is characterized in that the weight ratio between the concentration of the at least one hyaluronic acid [HA] and the concentration of the at least one local anesthetic [AL]: [HA]/[AL] is between 2 and 10/3; $2 \leq [HA]/[AL] \leq 10/3$.

In one embodiment, the injectable sterilized aqueous composition according to the invention is characterized in that the weight ratio between the concentration of the at least one hyaluronic acid [HA] and the concentration of the at least one local anesthetic [AL]: [HA]/[AL] is 20.

In one embodiment, the injectable sterilized aqueous composition according to the invention is characterized in that the weight ratio between the concentration of the at least one hyaluronic acid [HA] and the concentration of the at least one local anesthetic [AL]: [HA]/[AL] is 26/3.

In one embodiment, the injectable sterilized aqueous composition according to the invention is characterized in that the weight ratio between the concentration of the at least one hyaluronic acid [HA] and the concentration of the at least one local anesthetic [AL]: [HA]/[AL] is 20/3.

In one embodiment, the injectable sterilized aqueous composition according to the invention is characterized in that the weight ratio between the concentration of the at least one hyaluronic acid [HA] and the concentration of the at least one local anesthetic [AL]: [HA]/[AL] is 10/3.

In one embodiment, the injectable sterilized aqueous composition according to the invention is characterized in that the weight ratio between the concentration of the at least one hyaluronic acid [HA] and the concentration of the at least one local anesthetic [AL]: [HA]/[AL] is 7/3.

In one embodiment, the injectable sterilized aqueous composition according to the invention is characterized in that the weight ratio between the concentration of the at least one hyaluronic acid [HA] and the concentration of the at least one local anesthetic [AL]: [HA]/[AL] is 2.

In one embodiment, the injectable sterilized aqueous composition according to the invention is characterized in that the sterilization is carried out by heat, moist heat, gamma (γ) radiation, or by accelerated electron beam.

In one embodiment, the injectable sterilized aqueous composition according to the invention is characterized in that the sterilization step is carried out by heat.

In one embodiment, the injectable sterilized aqueous composition according to the invention is characterized in that the sterilization step is carried out by steam autoclaving.

In one embodiment, the injectable sterilized aqueous composition according to the invention is characterized in that the sterilization by steam autoclaving is carried out at a temperature of 121 to 134° C., for a time adapted to time adapted to the temperature.

For example, the sterilization by steam autoclaving is carried out at a temperature of between 127 and 130° C. for a period of between 1 and 20 min.

In one embodiment, the injectable sterilized aqueous composition according to the invention is characterized in that the sterilization step is carried out by irradiation with gamma (γ) radiation.

In one embodiment, the injectable sterilized aqueous composition according to the invention further comprises at least one additional compound.

In one embodiment, the injectable sterilized aqueous composition according to the invention is characterized in that the concentration of the at least one additional compound [CA] is between 0.1 and 100 mg/g of total weight of said composition.

In one embodiment, the injectable sterilized aqueous composition according to the invention is characterized in that the concentration of the at least one additional compound [CA] is between 1 and 50 mg/g of total weight of said composition.

In one embodiment, the injectable sterilized aqueous composition according to the invention is characterized in that the at least one additional compound is dimethyl sulfone, hereinafter DMS.

In one embodiment, the injectable sterilized aqueous composition according to the invention is characterized in that the at least one additional compound is a water-soluble salt of sucrose octasulfate, hereinafter SOS.

In one embodiment, the injectable sterilized aqueous composition according to the invention is characterized in that the at least one additional compound is a vitamin C derivative.

In one embodiment, the injectable sterilized aqueous composition according to the invention is characterized in that the at least one additional compound is a salt of magnesium ascorbyl phosphate, hereinafter MAP.

In one embodiment, the injectable sterilized aqueous composition according to the invention is characterized in that the at least one additional compound belongs to the catecholamine family.

In one embodiment, the injectable sterilized aqueous composition according to the invention is characterized in that the at least one additional compound belonging to the catecholamine family is epinephrine.

In one embodiment, the injectable sterilized aqueous composition according to the invention is characterized in that the concentration of the at least one additional compound [CA] is between 0.01% and 10% by weight relative to the total weight of said composition.

In one embodiment, the injectable sterilized aqueous composition according to the invention is characterized in that the concentration of the at least one additional compound [CA] is between 0.1% and 5% by weight relative to the total weight of said composition.

In one embodiment, the injectable sterilized aqueous composition according to the invention is characterized in that the at least one additional compound is dimethyl sulfone and the concentration thereof is between 1 and 10 mg/g of total weight of said composition.

In one embodiment, the injectable sterilized aqueous composition according to the invention is characterized in that the at least one additional compound is a water-soluble salt of sucrose octasulfate and the concentration thereof is between 1 and 40 mg/g of total weight of said composition.

In one embodiment, the injectable sterilized aqueous composition according to the invention is characterized in that the at least one additional compound is a salt of magnesium ascorbyl phosphate and the concentration thereof is between 0.3 and 20 mg/g of total weight of said composition.

In one embodiment, the injectable sterilized aqueous composition according to the invention is characterized in that the at least one local anesthetic is freely released in vivo.

The invention also relates to a process for adapting the rheological properties of a sterilized injectable aqueous composition comprising at least one hyaluronic acid and at least one polyol, which comprises the addition to said composition, before the sterilization step, of at least one local anesthetic chosen from the group consisting of benzocaine, chloroprocaine, procaine, etidocaine, aptocaine, chlorobutanol, diamocaine, dyclonine, guafecainol, polidocanol, mepivacaine, prilocaine, articaine, bupivacaine, ropivacaine, tetracaine and salts thereof and isolated isomers thereof.

In one embodiment, the process for adapting the rheological properties according to the invention is characterized in that the at least one local anesthetic is chosen from the group consisting of benzocaine, chloroprocaine, procaine, etidocaine, aptocaine, diamocaine, dyclonine, guafecainol, mepivacaine, prilocaine, articaine, bupivacaine, ropivacaine, tetracaine and salts thereof and isolated isomers thereof.

In one embodiment, the process for adapting the rheological properties according to the invention is characterized in that the at least one local anesthetic is chosen from the group consisting of benzocaine, chloroprocaine, procaine, etidocaine, aptocaine, diamocaine, mepivacaine, prilocaine, articaine, bupivacaine, ropivacaine, tetracaine and salts thereof and isolated isomers thereof.

In one embodiment, the process for adapting the rheological properties according to the invention is characterized in that the at least one local anesthetic is chosen from the group consisting of benzocaine, chloroprocaine, procaine, etidocaine and salts thereof.

In one embodiment, the process for adapting the rheological properties according to the invention is characterized in that the at least one local anesthetic is benzocaine.

In one embodiment, the process for adapting the rheological properties according to the invention is characterized in that the at least one local anesthetic is chloroprocaine.

In one embodiment, the process for adapting the rheological properties according to the invention is characterized in that the at least one local anesthetic is procaine.

In one embodiment, the process for adapting the rheological properties according to the invention is characterized in that the at least one local anesthetic is etidocaine.

In one embodiment, the process for adapting the rheological properties according to the invention is characterized in that the at least one local anesthetic is chosen from the group consisting of aptocaine, chlorobutanol, diamocaine, dyclonine, guafecainol, polidocanol, and salts thereof and isolated isomers.

In one embodiment, the process for adapting the rheological properties according to the invention is characterized in that the at least one local anesthetic is aptocaine.

In one embodiment, the process for adapting the rheological properties according to the invention is characterized in that the at least one local anesthetic is chlorobutanol.

In one embodiment, the process for adapting the rheological properties according to the invention is characterized in that the at least one local anesthetic is diamocaine.

In one embodiment, the process for adapting the rheological properties according to the invention is characterized in that the at least one local anesthetic is dyclonine.

In one embodiment, the process for adapting the rheological properties according to the invention is characterized in that the at least one local anesthetic is guafecainol.

In one embodiment, the process for adapting the rheological properties according to the invention is characterized in that the at least one local anesthetic is polidocanol.

In one embodiment, the process for adapting the rheological properties according to the invention is characterized in that the at least one local anesthetic is chosen from the group consisting of mepivacaine, prilocaine and salts thereof and isolated isomers thereof.

In one embodiment, the process for adapting the rheological properties according to the invention is characterized in that the at least one local anesthetic is mepivacaine.

In one embodiment, the process for adapting the rheological properties according to the invention is characterized in that the at least one local anesthetic is prilocaine.

In one embodiment, the process for adapting the rheological properties according to the invention is characterized in that the at least one local anesthetic is chosen from the group consisting of articaine, bupivacaine, ropivacaine, tetracaine and salts thereof and isolated isomers thereof.

In one embodiment, the process for adapting the rheological properties according to the invention is characterized in that the at least one local anesthetic is articaine.

In one embodiment, the process for adapting the rheological properties according to the invention is characterized in that the at least one local anesthetic is bupivacaine.

In one embodiment, the process for adapting the rheological properties according to the invention is characterized in that the at least one local anesthetic is ropivacaine.

In one embodiment, the process for adapting the rheological properties according to the invention is characterized in that the at least one local anesthetic is tetracaine.

In one embodiment, the process for adapting the rheological properties according to the invention is characterized in that the at least one hyaluronic acid is a non-crosslinked hyaluronic acid or a salt thereof, alone or as a mixture.

In one embodiment, the process for adapting the rheological properties according to the invention is characterized in that the at least one hyaluronic acid is a crosslinked hyaluronic acid or a salt thereof, alone or as a mixture.

In one embodiment, the process for adapting the rheological properties according to the invention is characterized in that the at least one crosslinked hyaluronic acid has a degree of crosslinking X of between 0.001 and 0.5.

In one embodiment, the process for adapting the rheological properties according to the invention is characterized in that the at least one crosslinked hyaluronic acid has a degree of crosslinking X of between 0.01 and 0.4.

In one embodiment, the process for adapting the rheological properties according to the invention is characterized in that the at least one crosslinked hyaluronic acid has a degree of crosslinking X of between 0.1 and 0.3.

In one embodiment, the process for adapting the rheological properties according to the invention is characterized in that the at least one crosslinked hyaluronic acid has a degree of crosslinking X of 0.06.

In one embodiment, the process for adapting the rheological properties according to the invention is characterized in that the at least one crosslinked hyaluronic acid has a degree of crosslinking X of 0.07.

In one embodiment, the process for adapting the rheological properties according to the invention is characterized in that the at least one crosslinked hyaluronic acid has a degree of crosslinking X of 0.12.

In one embodiment, the process for adapting the rheological properties according to the invention is characterized in that the molecular weight Mw of the at least one hyaluronic acid is in a range between 0.01 MDa and 5 MDa.

In one embodiment, the process for adapting the rheological properties according to the invention is characterized in that the molecular weight Mw of the at least one hyaluronic acid is in a range between 0.1 MDa and 3.5 MDa.

In one embodiment, the process for adapting the rheological properties according to the invention is characterized in that the molecular weight Mw of the at least one hyaluronic acid is in a range between 1 MDa and 3 MDa.

In one embodiment, the process for adapting the rheological properties according to the invention is characterized in that the molecular weight Mw of the at least one hyaluronic acid is in a range between 1 MDa and 2 MDa.

In one embodiment, the process for adapting the rheological properties according to the invention is characterized in that the molecular weight Mw of the at least one hyaluronic acid is 1 MDa.

In one embodiment, the process for adapting the rheological properties according to the invention is characterized in that the molecular weight Mw of the at least one hyaluronic acid is 2 MDa.

In one embodiment, the process for adapting the rheological properties according to the invention is characterized in that the molecular weight Mw of the at least one hyaluronic acid is 3 MDa.

In one embodiment, the process for adapting the rheological properties according to the invention is characterized in that said composition comprises at least one crosslinked or non-crosslinked hyaluronic acid chemically modified by substitution, or a salt thereof, alone or as a mixture.

In one embodiment, the injectable sterilized aqueous composition according to the invention comprises at least one doubly crosslinked hyaluronic acid as described in patent application WO 2000/046253 in the name of Fermentech Medical Limited.

In one embodiment, the injectable sterilized aqueous composition according to the invention comprises a mixture of crosslinked and non-crosslinked hyaluronic acids or a salt thereof.

In one embodiment, the injectable sterilized aqueous composition according to the invention comprises a mixture of crosslinked hyaluronic acids or a salt thereof.

In one embodiment, the mixture of crosslinked hyaluronic acids or a salt thereof is a single-phase mixture such as the one described in patent application WO 2009/071697 in the name of the applicant.

In one embodiment, the mixture of crosslinked hyaluronic acids or a salt thereof is a mixture obtained by mixing several hyaluronic acids, or a salt thereof, of different molecular weights prior to their crosslinking, as described in patent application WO 2004/092222 in the name of Corneal Industrie.

In one embodiment, the injectable sterilized aqueous composition according to the invention comprises at least one hyaluronic acid, or a salt thereof, substituted with a group providing lipophilic or hydrating properties, for instance the substituted hyaluronic acids as described in patent application FR 2 983 483 in the name of the applicant.

In one embodiment, the process for adapting the rheological properties according to the invention is characterized in that at least one hyaluronic acid is in the form of a sodium salt or of a potassium salt.

In one embodiment, the process for adapting the rheological properties according to the invention is characterized in that the at least one hyaluronic acid is a co-crosslinked hyaluronic acid or a salt thereof, alone or as a mixture.

In one embodiment, the process for adapting the rheological properties according to the invention is characterized in that the concentration of the at least one hyaluronic acid [HA] is between 2 mg/g and 50 mg/g of total weight of said composition.

In one embodiment, the process for adapting the rheological properties according to the invention is characterized in that the concentration of the at least one hyaluronic acid [HA] is between 4 mg/g and 40 mg/g of total weight of said composition.

In one embodiment, the process for adapting the rheological properties according to the invention is characterized in that the concentration of the at least one hyaluronic acid [HA] is between 5 mg/g and 30 mg/g of total weight of said composition.

In one embodiment, the process for adapting the rheological properties according to the invention is characterized in that the concentration of the at least one hyaluronic acid [HA] is between 10 mg/g and 30 mg/g of total weight of said composition.

In one embodiment, the process for adapting the rheological properties according to the invention is characterized in that the at least one hyaluronic acid [HA] is 20 mg/g of total weight of said composition.

In one embodiment, the process for adapting the rheological properties according to the invention is characterized in that the concentration of the at least one hyaluronic acid is between 0.2% and 5% by weight relative to the total weight of said composition.

In one embodiment, the process for adapting the rheological properties according to the invention is characterized in that the concentration of the at least one hyaluronic acid is greater than or equal to 1% by weight relative to the total weight of said composition.

In one embodiment, the process for adapting the rheological properties according to the invention is characterized in that the concentration of the at least one hyaluronic acid [HA] is 20 mg/g of total weight of said composition.

In one embodiment, the process for adapting the rheological properties according to the invention is characterized in that the at least one polyol is chosen from the group consisting of glycerol, sorbitol, propylene glycol, xylitol, mannitol, erythritol, maltitol and lactitol, alone or as a mixture.

In one embodiment, the process for adapting the rheological properties according to the invention is characterized in that the at least one polyol is chosen from the group consisting of mannitol, sorbitol, maltitol and glycerol, alone or as a mixture.

In one embodiment, the process for adapting the rheological properties according to the invention is characterized in that the at least one polyol is chosen from the group consisting of mannitol, sorbitol and maltitol, alone or as a mixture.

In one embodiment, the process for adapting the rheological properties according to the invention is characterized in that the at least one polyol is mannitol.

In one embodiment, the process for adapting the rheological properties according to the invention is characterized in that the at least one polyol is sorbitol.

In one embodiment, the process for adapting the rheological properties according to the invention is characterized in that the at least one polyol is maltitol.

In one embodiment, the process for adapting the rheological properties according to the invention is characterized in that the at least one polyol is glycerol.

In one embodiment, the process for adapting the rheological properties according to the invention is characterized in that said composition comprises at least mannitol and sorbitol.

In one embodiment, the process for adapting the rheological properties according to the invention is characterized in that said composition comprises at least mannitol and maltitol.

In one embodiment, the process for adapting the rheological properties according to the invention is characterized in that the concentration of the at least one polyol [Po] is between 0.01 mg/g and 50 mg/g.

In one embodiment, the process for adapting the rheological properties according to the invention is characterized in that the concentration of the at least one polyol [Po] is between 10 and 40 mg/g of total weight of said composition.

In one embodiment, the process for adapting the rheological properties according to the invention is characterized in that the concentration of the at least one polyol [Po] is between 15 and 30 mg/g of total weight of said composition.

In one embodiment, the process for adapting the rheological properties according to the invention is characterized in that the concentration of the at least one polyol [Po] is between 15 and 25 mg/g of total weight of said composition.

In one embodiment, the process for adapting the rheological properties according to the invention is characterized in that the concentration of the at least one polyol [Po] is between 20 and 40 mg/g of total weight of said composition.

In one embodiment, the process for adapting the rheological properties according to the invention is characterized in that the concentration of the at least one polyol [Po] is between 20 and 30 mg/g of total weight of said composition.

In one embodiment, the process for adapting the rheological properties according to the invention is characterized in that the concentration of the at least one polyol [Po] is between 25 and 35 mg/g of total weight of said composition.

In one embodiment, the process for adapting the rheological properties according to the invention is characterized in that the concentration of the at least one polyol [Po] is 35 mg/g of total weight of said composition.

In one embodiment, the process for adapting the rheological properties according to the invention is characterized in that the at least one polyol is mannitol and the concentration thereof is between 10 and 40 mg/g of total weight of said composition.

In one embodiment, the process for adapting the rheological properties according to the invention is characterized in that the at least one polyol is mannitol and the concentration thereof is between 15 and 30 mg/g of total weight of said composition.

In one embodiment, the process for adapting the rheological properties according to the invention is characterized in that the at least one polyol is mannitol and the concentration thereof is between 15 and 25 mg/g of total weight of said composition.

In one embodiment, the process for adapting the rheological properties according to the invention is characterized in that the at least one polyol is mannitol and the concentration thereof is between 20 and 40 mg/g of total weight of said composition.

In one embodiment, the process for adapting the rheological properties according to the invention is characterized in that the at least one polyol is mannitol and the concentration thereof is between 25 and 35 mg/g of total weight of said composition.

In one embodiment, the process for adapting the rheological properties according to the invention is characterized in that the at least one polyol is mannitol and the concentration thereof is 35 mg/g of total weight of said composition.

In one embodiment, the process for adapting the rheological properties according to the invention is characterized in that the at least one polyol is sorbitol and the concentration thereof is between 10 and 40 mg/g of total weight of said composition.

In one embodiment, the process for adapting the rheological properties according to the invention is characterized in that the at least one polyol is sorbitol and the concentration thereof is between 15 and 30 mg/g of total weight of said composition.

In one embodiment, the process for adapting the rheological properties according to the invention is characterized in that the at least one polyol is sorbitol and the concentration thereof is between 15 and 25 mg/g of total weight of said composition.

In one embodiment, the process for adapting the rheological properties according to the invention is characterized in that the at least one polyol is sorbitol and the concentration thereof is between 20 and 40 mg/g of total weight of said composition.

In one embodiment, the process for adapting the rheological properties according to the invention is characterized in that the at least one polyol is sorbitol and the concentration thereof is between 25 and 35 mg/g of total weight of said composition.

In one embodiment, the process for adapting the rheological properties according to the invention is characterized in that the at least one polyol is sorbitol and the concentration thereof is 35 mg/g of total weight of said composition.

In one embodiment, the process for adapting the rheological properties according to the invention is characterized in that the at least one polyol is maltitol and the concentration thereof is between 10 and 40 mg/g of total weight of said composition.

In one embodiment, the process for adapting the rheological properties according to the invention is characterized in that the at least one polyol is maltitol and the concentration thereof is between 15 and 30 mg/g of total weight of said composition.

In one embodiment, the process for adapting the rheological properties according to the invention is characterized in that the at least one polyol is maltitol and the concentration thereof is between 15 and 25 mg/g of total weight of said composition.

In one embodiment, the process for adapting the rheological properties according to the invention is characterized in that the at least one polyol is maltitol and the concentration thereof is between 20 and 40 mg/g of total weight of said composition.

In one embodiment, the process for adapting the rheological properties according to the invention is characterized in that the at least one polyol is maltitol and the concentration thereof is between 25 and 35 mg/g of total weight of said composition.

In one embodiment, the process for adapting the rheological properties according to the invention is characterized in that the at least one polyol is maltitol and the concentration thereof is 35 mg/g of total weight of said composition.

In one embodiment, the process for adapting the rheological properties according to the invention is characterized in that the at least one polyol is glycerol and the concentration thereof is between 10 and 40 mg/g of total weight of said composition.

In one embodiment, the process for adapting the rheological properties according to the invention is characterized in that the at least one polyol is glycerol and the concentration thereof is between 15 and 30 mg/g of total weight of said composition.

In one embodiment, the process for adapting the rheological properties according to the invention is characterized in that the at least one polyol is glycerol and the concentration thereof is between 15 and 25 mg/g of total weight of said composition.

In one embodiment, the process for adapting the rheological properties according to the invention is characterized in that the at least one polyol is glycerol and the concentration thereof is between 20 and 40 mg/g of total weight of said composition.

In one embodiment, the process for adapting the rheological properties according to the invention is characterized in that the at least one polyol is glycerol and the concentration thereof is between 25 and 35 mg/g of total weight of said composition.

In one embodiment, the process for adapting the rheological properties according to the invention is characterized in that the at least one polyol is glycerol and the concentration thereof is 35 mg/g of total weight of said composition.

In one embodiment, the process for adapting the rheological properties according to the invention is characterized in that the concentration of the at least one local anesthetic [AL] is between 0.01 mg/g and 50 mg/g of total weight of said composition.

In one embodiment, the process for adapting the rheological properties according to the invention is characterized in that the concentration of the at least one local anesthetic [AL] is between 0.05 mg/g and 45 mg/g of total weight of said composition.

In one embodiment, the process for adapting the rheological properties according to the invention is characterized in that the concentration of the at least one local anesthetic [AL] is between 0.1 mg/g and 40 mg/g of total weight of said composition.

In one embodiment, the process for adapting the rheological properties according to the invention is characterized in that the concentration of the at least one local anesthetic [AL] is between 0.2 mg/g and 30 mg/g of total weight of said composition.

In one embodiment, the process for adapting the rheological properties according to the invention is characterized in that the concentration of the at least one local anesthetic [AL] is between 0.5 mg/g and 20 mg/g of total weight of said composition.

In one embodiment, the process for adapting the rheological properties according to the invention is characterized in that the concentration of the at least one local anesthetic [AL] is between 1 mg/g and 15 mg/g of total weight of said composition.

In one embodiment, the process for adapting the rheological properties according to the invention is characterized in that the concentration of the at least one local anesthetic [AL] is between 1 mg/g and 10 mg/g of total weight of said composition.

In one embodiment, the process for adapting the rheological properties according to the invention is characterized in that the concentration of the at least one local anesthetic [AL] is between 1 mg/g and 6 mg/g of total weight of said composition.

In one embodiment, the process for adapting the rheological properties according to the invention is characterized in that the concentration of the at least one local anesthetic [AL] is between 1 mg/g and 5 mg/g of total weight of said composition.

In one embodiment, the process for adapting the rheological properties according to the invention is characterized in that the concentration of the at least one local anesthetic [AL] is between 2 mg/g and 5 mg/g of total weight of said composition.

In one embodiment, the process for adapting the rheological properties according to the invention is characterized in that the concentration of the at least one local anesthetic [AL] is between 6 mg/g and 10 mg/g of total weight of said composition.

In one embodiment, the process for adapting the rheological properties according to the invention is characterized in that the concentration of the at least one local anesthetic [AL] is 1 mg/g of total weight of said composition.

In one embodiment, the process for adapting the rheological properties according to the invention is characterized in that the concentration of the at least one local anesthetic [AL] is 3 mg/g of total weight of said composition.

In one embodiment, the process for adapting the rheological properties according to the invention is characterized in that the concentration of the at least one local anesthetic [AL] is 4 mg/g of total weight of said composition.

In one embodiment, the process for adapting the rheological properties according to the invention is characterized in that the concentration of the at least one local anesthetic [AL] is 5 mg/g of total weight of said composition.

In one embodiment, the process for adapting the rheological properties according to the invention is characterized in that the concentration of the at least one local anesthetic [AL] is 6 mg/g of total weight of said composition.

In one embodiment, the process for adapting the rheological properties according to the invention is characterized in that the concentration of the at least one local anesthetic [AL] is 10 mg/g of total weight of said composition.

In one embodiment, the process for adapting the rheological properties according to the invention is characterized in that the at least one local anesthetic is benzocaine [BENZ], and wherein the concentration of benzocaine [BENZ] is between 0.01 mg/g and 50 mg/g of total weight of said composition.

In one embodiment, the process for adapting the rheological properties according to the invention is characterized in that the at least one local anesthetic is benzocaine [BENZ], and wherein the concentration of benzocaine [BENZ] is between 1 mg/g and 15 mg/g of total weight of said composition.

In one embodiment, the process for adapting the rheological properties according to the invention is characterized in that the at least one local anesthetic is benzocaine [BENZ], and wherein the concentration of benzocaine [BENZ] is between 1 mg/g and 6 mg/g of total weight of said composition.

In one embodiment, the process for adapting the rheological properties according to the invention is characterized in that the at least one local anesthetic is benzocaine [BENZ], and wherein the concentration of benzocaine [BENZ] is approximately 3 mg/g of total weight of said composition.

In one embodiment, the process for adapting the rheological properties according to the invention is characterized in that the at least one local anesthetic is chloroprocaine [CHPR], and wherein the concentration of chloroprocaine [CHPR] is between 0.01 mg/g and 50 mg/g of total weight of said composition.

In one embodiment, the process for adapting the rheological properties according to the invention is characterized in that the at least one local anesthetic is chloroprocaine [CHPR], and wherein the concentration of chloroprocaine [CHPR] is between 1 mg/g and 15 mg/g of total weight of said composition.

In one embodiment, the process for adapting the rheological properties according to the invention is characterized in that the at least one local anesthetic is chloroprocaine [CHPR], and wherein the concentration of chloroprocaine [CHPR] is between 1 mg/g and 6 mg/g of total weight of said composition.

In one embodiment, the process for adapting the rheological properties according to the invention is characterized in that the at least one local anesthetic is chloroprocaine [CHPR], and wherein the concentration of chloroprocaine [CHPR] is approximately 3 mg/g of total weight of said composition.

In one embodiment, the process for adapting the rheological properties according to the invention is characterized in that the at least one local anesthetic is procaine [PROC], and wherein the concentration of procaine [PROC] is between 0.01 mg/g and 50 mg/g of total weight of said composition.

In one embodiment, the process for adapting the rheological properties according to the invention is characterized in that the at least one local anesthetic is procaine [PROC], and wherein the concentration of procaine [PROC] is between 1 mg/g and 15 mg/g of total weight of said composition.

In one embodiment, the process for adapting the rheological properties according to the invention is characterized in that the at least one local anesthetic is procaine [PROC], and wherein the concentration of procaine [PROC] is between 1 mg/g and 6 mg/g of total weight of said composition.

In one embodiment, the process for adapting the rheological properties according to the invention is characterized in that the at least one local anesthetic is procaine [PROC], and wherein the concentration of procaine [PROC] is approximately 3 mg/g of total weight of said composition.

In one embodiment, the process for adapting the rheological properties according to the invention is characterized in that the at least one local anesthetic is etidocaine [ETID], and wherein the concentration of etidocaine [ETID] is between 0.01 mg/g and 50 mg/g of total weight of said composition.

In one embodiment, the process for adapting the rheological properties according to the invention is characterized in that the at least one local anesthetic is etidocaine [ETID], and wherein the concentration of etidocaine [ETID] is between 1 mg/g and 15 mg/g of total weight of said composition.

In one embodiment, the process for adapting the rheological properties according to the invention is characterized in that the at least one local anesthetic is etidocaine [ETID], and wherein the concentration of etidocaine [ETID] is between 1 mg/g and 6 mg/g of total weight of said composition.

In one embodiment, the process for adapting the rheological properties according to the invention is characterized in that the at least one local anesthetic is etidocaine [ETID], and wherein the concentration of etidocaine [ETID] is approximately 3 mg/g of total weight of said composition.

In one embodiment, the process for adapting the rheological properties according to the invention is characterized in that the at least one local anesthetic is aptocaine [APTO], and wherein the concentration of aptocaine [APTO] is between 0.01 mg/g and 50 mg/g of total weight of said composition.

In one embodiment, the process for adapting the rheological properties according to the invention is characterized in that the at least one local anesthetic is aptocaine [APTO], and wherein the concentration of aptocaine [APTO] is between 1 mg/g and 15 mg/g of total weight of said composition.

In one embodiment, the process for adapting the rheological properties according to the invention is characterized in that the at least one local anesthetic is aptocaine [APTO], and wherein the concentration of aptocaine [APTO] is between 1 mg/g and 6 mg/g of total weight of said composition.

In one embodiment, the process for adapting the rheological properties according to the invention is characterized in that the at least one local anesthetic is aptocaine [APTO], and wherein the concentration of aptocaine [APTO] is approximately 3 mg/g of total weight of said composition.

In one embodiment, the process for adapting the rheological properties according to the invention is characterized in that the at least one local anesthetic is chlorobutanol [CHLO], and wherein the concentration of chlorobutanol [CHLO] is between 0.01 mg/g and 50 mg/g of total weight of said composition.

In one embodiment, the process for adapting the rheological properties according to the invention is characterized in that the at least one local anesthetic is chlorobutanol [CHLO], and wherein the concentration of chlorobutanol [CHLO] is between 1 mg/g and 15 mg/g of total weight of said composition.

In one embodiment, the process for adapting the rheological properties according to the invention is characterized in that the at least one local anesthetic is chlorobutanol [CHLO], and wherein the concentration of chlorobutanol [CHLO] is between 1 mg/g and 6 mg/g of total weight of said composition.

In one embodiment, the process for adapting the rheological properties according to the invention is characterized in that the at least one local anesthetic is chlorobutanol [CHLO], and wherein the concentration of chlorobutanol [CHLO] is approximately 3 mg/g of total weight of said composition.

In one embodiment, the process for adapting the rheological properties according to the invention is characterized in that the at least one local anesthetic is diamocaine [DIAM], and wherein the concentration of diamocaine [DIAM] is between 0.01 mg/g and 50 mg/g of total weight of said composition.

In one embodiment, the process for adapting the rheological properties according to the invention is characterized in that the at least one local anesthetic is diamocaine [DIAM], and wherein the concentration of diamocaine [DIAM] is between 1 mg/g and 15 mg/g of total weight of said composition.

In one embodiment, the process for adapting the rheological properties according to the invention is characterized in that the at least one local anesthetic is diamocaine [DIAM], and wherein the concentration of diamocaine [DIAM] is between 1 mg/g and 6 mg/g of total weight of said composition.

In one embodiment, the process for adapting the rheological properties according to the invention is characterized in that the at least one local anesthetic is diamocaine [DIAM], and wherein the concentration of diamocaine [DIAM] is approximately 3 mg/g of total weight of said composition.

In one embodiment, the process for adapting the rheological properties according to the invention is characterized in that the at least one local anesthetic is dyclonine [DYCL], and wherein the concentration of dyclonine [DYCL] is between 0.01 mg/g and 50 mg/g of total weight of said composition.

In one embodiment, the process for adapting the rheological properties according to the invention is characterized in that the at least one local anesthetic is dyclonine [DYCL], and wherein the concentration of dyclonine [DYCL] is between 1 mg/g and 15 mg/g of total weight of said composition.

In one embodiment, the process for adapting the rheological properties according to the invention is characterized in that the at least one local anesthetic is dyclonine [DYCL], and wherein the concentration of dyclonine [DYCL] is between 1 mg/g and 6 mg/g of total weight of said composition.

In one embodiment, the process for adapting the rheological properties according to the invention is characterized in that the at least one local anesthetic is dyclonine [DYCL], and wherein the concentration of dyclonine [DYCL] is approximately 3 mg/g of total weight of said composition.

In one embodiment, the process for adapting the rheological properties according to the invention is characterized in that the at least one local anesthetic is guafecainol

[GUAF], and wherein the concentration of guafecainol [GUAF] is between 0.01 mg/g and 50 mg/g of total weight of said composition.

In one embodiment, the process for adapting the rheological properties according to the invention is characterized in that the at least one local anesthetic is guafecainol [GUAF], and wherein the concentration of guafecainol [GUAF] is between 1 mg/g and 15 mg/g of total weight of said composition.

In one embodiment, the process for adapting the rheological properties according to the invention is characterized in that the at least one local anesthetic is guafecainol [GUAF], and wherein the concentration of guafecainol [GUAF] is between 1 mg/g and 6 mg/g of total weight of said composition.

In one embodiment, the process for adapting the rheological properties according to the invention is characterized in that the at least one local anesthetic is guafecainol [GUAF], and wherein the concentration of guafecainol [GUAF] is approximately 3 mg/g of total weight of said composition.

In one embodiment, the process for adapting the rheological properties according to the invention is characterized in that the at least one local anesthetic is polidocanol [POLI], and wherein the concentration of polidocanol [POLI] is between 0.01 mg/g and 50 mg/g of total weight of said composition.

In one embodiment, the process for adapting the rheological properties according to the invention is characterized in that the at least one local anesthetic is polidocanol [POLI], and wherein the concentration of polidocanol [POLI] is between 1 mg/g and 15 mg/g of total weight of said composition.

In one embodiment, the process for adapting the rheological properties according to the invention is characterized in that the at least one local anesthetic is polidocanol [POLI], and wherein the concentration of polidocanol [POLI] is between 1 mg/g and 6 mg/g of total weight of said composition.

In one embodiment, the process for adapting the rheological properties according to the invention is characterized in that the at least one local anesthetic is polidocanol [POLI], and wherein the concentration of polidocanol [POLI] is approximately 3 mg/g of total weight of said composition.

In one embodiment, the process for adapting the rheological properties according to the invention is characterized in that the at least one local anesthetic is mepivacaine [MEPI], and wherein the concentration of mepivacaine [MEPI] is between 0.01 mg/g and 50 mg/g of total weight of said composition.

In one embodiment, the process for adapting the rheological properties according to the invention is characterized in that the at least one local anesthetic is mepivacaine [MEPI], and wherein the concentration of mepivacaine [MEPI] is between 1 mg/g and 15 mg/g of total weight of said composition.

In one embodiment, the process for adapting the rheological properties according to the invention is characterized in that the at least one local anesthetic is mepivacaine [MEPI], and wherein the concentration of mepivacaine [MEPI] is between 1 mg/g and 6 mg/g of total weight of said composition.

In one embodiment, the process for adapting the rheological properties according to the invention is characterized in that the at least one local anesthetic is mepivacaine [MEPI], and wherein the concentration of mepivacaine [MEPI] is approximately 3 mg/g of total weight of said composition.

In one embodiment, the process for adapting the rheological properties according to the invention is characterized in that the at least one local anesthetic is prilocaine [PRILO], and wherein the concentration of prilocaine [PRILO] is between 0.01 mg/g and 50 mg/g of total weight of said composition.

In one embodiment, the process for adapting the rheological properties according to the invention is characterized in that the at least one local anesthetic is prilocaine [PRILO], and wherein the concentration of prilocaine [PRILO] is between 1 mg/g and 15 mg/g of total weight of said composition.

In one embodiment, the process for adapting the rheological properties according to the invention is characterized in that the at least one local anesthetic is prilocaine [PRILO], and wherein the concentration of prilocaine [PRILO] is between 1 mg/g and 6 mg/g of total weight of said composition.

In one embodiment, the process for adapting the rheological properties according to the invention is characterized in that the at least one local anesthetic is prilocaine [PRILO], and wherein the concentration of prilocaine [PRILO] is approximately 3 mg/g of total weight of said composition.

In one embodiment, the process for adapting the rheological properties according to the invention is characterized in that the at least one local anesthetic is articaine [ARTI], and wherein the concentration of articaine [ARTI] is between 0.01 mg/g and 50 mg/g of total weight of said composition.

In one embodiment, the process for adapting the rheological properties according to the invention is characterized in that the at least one local anesthetic is articaine [ARTI], and wherein the concentration of articaine [ARTI] is between 1 mg/g and 15 mg/g of total weight of said composition.

In one embodiment, the process for adapting the rheological properties according to the invention is characterized in that the at least one local anesthetic is articaine [ARTI], and wherein the concentration of articaine [ARTI] is between 1 mg/g and 6 mg/g of total weight of said composition.

In one embodiment, the process for adapting the rheological properties according to the invention is characterized in that the at least one local anesthetic is articaine [ARTI], and wherein the concentration of articaine [ARTI] is approximately 3 mg/g of total weight of said composition.

In one embodiment, the process for adapting the rheological properties according to the invention is characterized in that the at least one local anesthetic is bupivacaine [BUPI], and wherein the concentration of bupivacaine [BUPI] is between 0.01 mg/g and 50 mg/g of total weight of said composition.

In one embodiment, the process for adapting the rheological properties according to the invention is characterized in that the at least one local anesthetic is bupivacaine [BUPI], and wherein the concentration of bupivacaine [BUPI] is between 1 mg/g and 15 mg/g of total weight of said composition.

In one embodiment, the process for adapting the rheological properties according to the invention is characterized in that the at least one local anesthetic is bupivacaine [BUPI], and wherein the concentration of bupivacaine [BUPI] is between 1 mg/g and 6 mg/g of total weight of said composition.

In one embodiment, the process for adapting the rheological properties according to the invention is characterized in that the at least one local anesthetic is bupivacaine [BUPI], and wherein the concentration of bupivacaine [BUPI] is approximately 3 mg/g of total weight of said composition.

In one embodiment, the process for adapting the rheological properties according to the invention is characterized in that the at least one local anesthetic is ropivacaine [ROPI], and wherein the concentration of ropivacaine [ROPI] is between 0.01 mg/g and 50 mg/g of total weight of said composition.

In one embodiment, the process for adapting the rheological properties according to the invention is characterized in that the at least one local anesthetic is ropivacaine [ROPI], and wherein the concentration of ropivacaine [ROPI] is between 1 mg/g and 15 mg/g of total weight of said composition.

In one embodiment, the process for adapting the rheological properties according to the invention is characterized in that the at least one local anesthetic is ropivacaine [ROPI], and wherein the concentration of ropivacaine [ROPI] is between 1 mg/g and 6 mg/g of total weight of said composition.

In one embodiment, the process for adapting the rheological properties according to the invention is characterized in that the at least one local anesthetic is ropivacaine [ROPI], and wherein the concentration of ropivacaine [ROPI] is approximately 3 mg/g of total weight of said composition.

In one embodiment, the process for adapting the rheological properties according to the invention is characterized in that the at least one local anesthetic is tetracaine [TETRA], and wherein the concentration of tetracaine [TETRA] is between 0.01 mg/g and 50 mg/g of total weight of said composition.

In one embodiment, the process for adapting the rheological properties according to the invention is characterized in that the at least one local anesthetic is tetracaine [TETRA], and wherein the concentration of tetracaine [TETRA] is between 1 mg/g and 15 mg/g of total weight of said composition.

In one embodiment, the process for adapting the rheological properties according to the invention is characterized in that the at least one local anesthetic is tetracaine [TETRA], and wherein the concentration of tetracaine [TETRA] is between 1 mg/g and 6 mg/g of total weight of said composition.

In one embodiment, the process for adapting the rheological properties according to the invention is characterized in that the at least one local anesthetic is tetracaine [TETRA], and wherein the concentration of tetracaine [TETRA] is approximately 3 mg/g of total weight of said composition.

In one embodiment, the process for adapting the rheological properties according to the invention is characterized in that the weight ratio between the concentration of the at least one polyol [Po] and the concentration of the at least one local anesthetic [AL]: [Po]/[AL] is between 0.0002 and 5000; $0.0002 \leq [Po]/[AL] \leq 5000$.

In one embodiment, the process for adapting the rheological properties according to the invention is characterized in that the weight ratio between the concentration of the at least one polyol [Po] and the concentration of the at least one local anesthetic [AL]: [Po]/[AL] is between 0.002 and 500; $0.002 \leq [Po]/[AL] \leq 500$.

In one embodiment, the process for adapting the rheological properties according to the invention is characterized in that the weight ratio between the concentration of the at least one polyol [Po] and the concentration of the at least one local anesthetic [AL]: [Po]/[AL] is between 0.02 and 50; $0.02 \leq [Po]/[AL] \leq 50$.

In one embodiment, the process for adapting the rheological properties according to the invention is characterized in that the weight ratio between the concentration of the at least one polyol [Po] and the concentration of the at least one local anesthetic [AL]: [Po]/[AL] is between 1 and 20; $1 \leq [Po]/[AL] \leq 20$.

In one embodiment, the process for adapting the rheological properties according to the invention is characterized in that the weight ratio between the concentration of the at least one polyol [Po] and the concentration of the at least one local anesthetic [AL]: [Po]/[AL] is between 3 and 15; $3 \leq [Po]/[AL] \leq 15$.

In one embodiment, the process for adapting the rheological properties according to the invention is characterized in that the weight ratio between the concentration of the at least one polyol [Po] and the concentration of the at least one local anesthetic [AL]: [Po]/[AL] is between 4 and 8; $4 \leq [Po]/[AL] \leq 8$.

In one embodiment, the process for adapting the rheological properties according to the invention is characterized in that the weight ratio between the concentration of the at least one polyol [Po] and the concentration of the at least one local anesthetic [AL]: [Po]/[AL] is between 10 and 13; $10 \leq [Po]/[AL] \leq 13$.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is between 0.1 and 50; $0.1 \leq [HA]/[AL] \leq 50$.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is between 0.5 and 40; $0.5 \leq [HA]/[AL] \leq 40$.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is between 1 and 30; $1 \leq [HA]/[AL] \leq 30$.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is between 2 and 20; $2 \leq [HA]/[AL] \leq 20$.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is between 7/3 and 26/3; $7/3 \leq [HA]/[AL] \leq 26/3$.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is between 2 and 20/3; $2 \leq [HA]/[AL] \leq 20/3$.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is between 2 and 10/3; 2≤[HA]/[AL]≤10/3.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is 20.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is 26/3.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is 20/3.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is 10/3.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is 7/3.

In one embodiment, the process for adapting the rheological properties according to the invention is characterized in that the weight ratio between the concentration of the at least one hyaluronic acid [HA] and the concentration of the at least one local anesthetic [AL]: [HA]/[AL] is 2.

In one embodiment, the process for adapting the rheological properties according to the invention is characterized in that the sterilization step is carried out by heat, moist heat, gamma (γ), radiation, or by accelerated electron beam.

In one embodiment, the process for adapting the rheological properties according to the invention is characterized in that the sterilization step is carried out by steam autoclaving.

In one embodiment, the process for adapting the rheological properties according to the invention is characterized in that the sterilization by steam autoclaving is carried out at a temperature of 121 to 134° C., for a time adapted to the temperature.

For example, the sterilization by steam autoclaving is carried out at a temperature of between 127 and 130° C. for a period of between 1 and 20 min.

In one embodiment, the process for adapting the rheological properties according to the invention is characterized in that the sterilization step is carried out by irradiation with gamma (γ) radiation.

In one embodiment, the process for adapting the rheological properties according to the invention is characterized in that said composition further comprises at least one additional compound.

In one embodiment, the process for adapting the rheological properties according to the invention is characterized in that the concentration of the at least one additional compound [CA] is between 0.1 and 100 mg/g of total weight of said composition.

In one embodiment, the process for adapting the rheological properties according to the invention is characterized in that the concentration of the at least one additional compound [CA] is between 1 and 50 mg/g of total weight of said composition.

In one embodiment, the process for adapting the rheological properties according to the invention is characterized in that the at least one additional compound is dimethyl sulfone, hereinafter DMS.

In one embodiment, the process for adapting the rheological properties according to the invention is characterized in that the at least one additional compound is a water-soluble salt of sucrose octasulfate, hereinafter SOS.

In one embodiment, the process for adapting the rheological properties according to the invention is characterized in that the at least one additional compound is a vitamin C derivative.

In one embodiment, the process for adapting the rheological properties according to the invention is characterized in that the at least one additional compound is a salt of magnesium ascorbyl phosphate, hereinafter MAP.

In one embodiment, the process for adapting the rheological properties according to the invention is characterized in that the at least one additional compound belongs to the catecholamine family.

In one embodiment, the process for adapting the rheological properties according to the invention is characterized in that the at least one additional compound belonging to the catecholamine family is epinephrine.

In one embodiment, the process for adapting the rheological properties according to the invention is characterized in that the concentration of the at least one additional compound [CA] is between 0.01% and 10% by weight relative to the total weight of said composition.

In one embodiment, the process for adapting the rheological properties according to the invention is characterized in that the concentration of the at least one additional compound [CA] is between 0.1% and 5% by weight relative to the total weight of said composition.

In one embodiment, the process for adapting the rheological properties according to the invention is characterized in that the at least one additional compound is dimethyl sulfone and the concentration thereof is between 1 and 10 mg/g of total weight of said composition.

In one embodiment, the process for adapting the rheological properties according to the invention is characterized in that the at least one additional compound is a water-soluble salt of sucrose octasulfate and the concentration thereof is between 1 and 40 mg/g of total weight of said composition.

In one embodiment, the process for adapting the rheological properties according to the invention is characterized in that the at least one additional compound is a salt of magnesium ascorbyl phosphate and the concentration thereof is between 0.3 and 20 mg/g of total weight of said composition.

In one embodiment, the process for adapting the rheological properties according to the invention is characterized in that the at least one local anesthetic is freely released in vivo.

The invention also relates to a process for producing an injectable sterilized aqueous composition according to the invention, which comprises at least the following steps:
1) a step of hydration in a buffer solution at a pH close to physiological pH of the fibers of at least one hyaluronic acid or a salt thereof, alone or as a mixture, so as to obtain a hydrogel;
2) a step of incorporation of at least one polyol in aqueous solution into the hydrogel obtained in the previous step;
3) a step of incorporation of at least one local anesthetic chosen from the group consisting of benzocaine, chloroprocaine, procaine, etidocaine, aptocaine, chlorobutanol, diamocaine, dyclonine, guafecainol, polidocanol, mepivacaine, prilocaine, articaine, bupivacaine, ropivacaine and tetracaine and salts thereof and isolated isomers thereof, into the hydrogel obtained in the previous step;

4) a homogenization step; and
5) a sterilization step;

it being possible for said steps 2) and 3) to be carried out in any order or simultaneously.

In one embodiment, the process according to the invention is characterized in that the at least one local anesthetic is incorporated in solid form.

In one embodiment, the process according to the invention is characterized in that the at least one local anesthetic is incorporated in powder form.

In one embodiment, the process according to the invention is characterized in that the at least one local anesthetic is incorporated in the form of the solution.

In one embodiment, the process according to the invention is characterized in that the hyaluronic acid is in the form of fibers.

In one embodiment, the process according to the invention is characterized in that the hyaluronic acid is in the form of paillettes.

In one embodiment, the process according to the invention is characterized in that the buffer solution is an aqueous solution of phosphate buffer.

In one embodiment, the process according to the invention is characterized in that the pH of the solution of at least one local anesthetic is adjusted to a value of between 6.5 and 7 before it is introduced into the gel and/or hydrogel.

In one embodiment, the process according to the invention is characterized in that the pH of the gel and/or hydrogel is adjusted to a value of between 7.7 and 8 before the incorporation of at least one local anesthetic, the pH of which is not adjusted.

In one embodiment, the process according to the invention is characterized in that the solution of at least one local anesthetic is incorporated into the gel according to the process described in patent application WO 2010/015901 in the name of Allergan.

In one embodiment, the process according to the invention is characterized in that the hydration step is carried out at ambient temperature.

In one embodiment, the process according to the invention is characterized in that the homogenization step is carried out at ambient temperature.

In one embodiment, the process according to the invention further comprises at least one step of packaging the homogenized mixture in syringes.

In one embodiment, the process according to the invention further comprises at least one step of packaging the homogenized mixture in single-dose bottles.

In one embodiment, the process according to the invention comprises at least one sterilization step.

In one embodiment, the process according to the invention is characterized in that the sterilization step is carried out after the packaging step.

In one embodiment, the process according to the invention is characterized in that the sterilization step is carried out by heat, moist heat, gamma (γ) radiation or by accelerated electron beam.

In one embodiment, the process according to the invention is characterized in that said sterilization step is carried out by heat.

In one embodiment, the process according to the invention is one in which said sterilization step is carried out by steam autoclaving.

In one embodiment, the process according to the invention is characterized in that said sterilization step is carried out after the packaging by steam autoclaving.

In one embodiment, the process according to the invention is characterized in that said sterilization step is carried out after the packaging, by irradiation with gamma (γ) radiation or by accelerated electron beam.

In one embodiment, the process according to the invention is characterized in that the sterilization by steam autoclaving is carried out after the packaging, at a temperature of 121 to 134° C., for a time adapted to the temperature.

For example, the sterilization by steam autoclaving is carried out at a temperature of between 127 and 130° C. for a period of between 1 and 20 min.

In one embodiment, the process according to the invention further comprises at least one crosslinking step.

In one embodiment, the process according to the invention further comprises at least one crosslinking step simultaneously with or subsequent to step 1.

In one embodiment, the process according to the invention further comprises at least one crosslinking step simultaneously with step 1.

In one embodiment, the process according to the invention further comprises at least one crosslinking step subsequent to step 1.

In one embodiment, the process according to the invention is characterized in that at least one crosslinking step lies between the hydration step and the step of incorporating at least one local anesthetic.

In one embodiment, the process according to the invention is characterized in that at least one crosslinking step is carried out by means of at least one crosslinking agent.

In one embodiment, the process according to the invention is characterized in that the at least one crosslinking agent is bifunctional or polyfunctional.

In one embodiment, the process according to the invention is characterized in that the at least one bifunctional or polyfunctional crosslinking agent is chosen from the group consisting of ethylene glycol diglycidyl ether, butanediol diglycidyl ether (BDDE), polyglycerol polyglycidyl ether, polyethylene glycol diglycidyl ether, polypropylene glycol diglycidyl ether, a bis- or polyepoxy such as 1,2,3,4-diepoxybutane or 1,2,7,8-diepoxyoctane, a dialkyl sulfone, divinyl sulfone, formaldehyde, epichlorohydrin or else glutaraldehyde, and carbodiimides such as, for example, 1-ethyl-3-[3-dimethylaminopropyl]carbodiimide hydrochloride (EDC).

In one embodiment, the process according to the invention is characterized in that the at least one bifunctional crosslinking agent is butanediol diglycidyl ether (BDDE) or 1,2,7,8-diepoxyoctane.

In one embodiment, the production process according to the invention is characterized in that the crosslinking step is carried out according to the techniques known to those skilled in the art.

In one embodiment, the process according to the invention comprises, after the crosslinking step, at least one purification and washing step carried out according to the techniques known to those skilled in the art.

In one embodiment, the process according to the invention further comprises at least one step of incorporating at least one polyol.

In one embodiment, the process according to the invention is characterized in that the polyols are chosen from the group consisting of glycerol, sorbitol, propylene glycol, xylitol, mannitol, erythritol, maltitol and lactitol, alone or as a mixture.

In one embodiment, the process according to the invention further comprises at least one step of mixing a solution of at least one additional compound with the hydrogel obtained in the hydration step.

In one embodiment, the process according to the invention is characterized in that the step of mixing a solution of at least one additional compound with the hydrogel obtained in the hydration step comes before the homogenization step.

In one embodiment, the process according to the invention is characterized in that the step of mixing a solution of at least one additional compound with the hydrogel obtained in the hydration step is carried out at a temperature suitable for the production process. In one embodiment, it is carried out at ambient temperature.

The invention also relates to the use of an injectable sterilized aqueous composition according to the invention, for the formulation of a composition for filling in wrinkles, or for correcting skin defects or volume defects (cheek bones, chin, lips).

Given that the use relates to an injectable sterilized aqueous composition according to the invention, all of the embodiments applicable to the injectable sterilized aqueous composition according to the invention are applicable to the use of the injectable sterilized aqueous composition according to the invention, for the formulation of a composition for filling in wrinkles, or for correcting skin defects or volume defects (cheek bones, chin, lips).

The invention also relates to the use of an injectable sterilized aqueous composition according to the invention, for the formulation of a composition that can be injected into a joint to replace or supplement deficient synovial fluid.

Given that the use relates to an injectable sterilized aqueous composition according to the invention, all of the embodiments applicable to the injectable sterilized aqueous composition according to the invention are applicable to the use of the injectable sterilized aqueous composition according to the invention, for the formulation of a composition that can be injected into a joint to replace or supplement deficient synovial fluid.

The invention also relates to an injectable sterilized aqueous composition according to the invention, for use in replacing or supplementing deficient synovial fluid.

The invention also relates to a kit comprising an injectable sterilized aqueous composition according to the invention, packaged in syringes and sterilized after packaging.

The invention also relates to a kit comprising an injectable sterilized aqueous composition according to the invention, packaged in single-dose bottles and sterilized after packaging.

Given that the kit comprises an injectable sterilized aqueous composition according to the invention, all of the embodiments applicable to the injectable sterilized aqueous composition according to the invention are applicable to the kit comprising an injectable sterilized aqueous composition according to the invention, packaged in syringes or in single-dose bottles and sterilized after packaging.

The invention also relates to the use of an injectable sterilized aqueous composition according to the invention, for the formulation of a composition for filling in wrinkles, or for correcting skin defects or volume defects (cheek bones, chin, lips).

The invention also relates to an injectable sterilized aqueous composition according to the invention, for use in filling in wrinkles and/or in correcting skin defects.

The invention also relates to the use of an injectable sterilized aqueous composition according to the invention, for the formulation of a composition that can be injected into a joint to replace or supplement deficient synovial fluid.

The invention also relates to an injectable sterilized aqueous composition according to the invention, for use in replacing or supplementing deficient synovial fluid.

The invention also relates to the use of an injectable sterilized aqueous composition according to the invention, for the formulation of a composition for filling in wrinkles.

The invention also relates to the use of an injectable sterilized aqueous composition according to the invention, for the formulation of a viscosupplementation composition.

The invention also relates to an injectable sterilized aqueous composition according to the invention, for use as a medicament.

The applications targeted are more particularly the applications commonly observed in the context of injectable viscoelastic products and polysaccharides used or potentially useable in the following pathological conditions or treatments:
  esthetic injections in the face: for filling in wrinkles, skin defects or volume defects (cheek bones, chin, lips);
  volumizing injections in the body: breast and buttock augmentation, G-spot augmentation, vaginoplastie, reconstruction of the vaginal labia, penis enlargement;
  treatment for arthrosis, injection into the joint to replace or supplement deficient synovial fluid;
  peri-urethral injection for the treatment of urinal incontinence caused by sphincter insufficiency;
  post-surgical injection for preventing peritoneal adhesions in particular;
  injection following surgery for long-sightedness by scleral laser incisions;
  injection into the vitreous cavity;
  injection during cataract surgery;
  injection into genital parts.

More particularly, in esthetic surgery, according to its viscoelastic properties and persistence properties, the injectable sterilized aqueous composition obtained according to the process of the invention may be used:
  for filling in fine, moderate or deep wrinkles, and may be injected using narrow-diameter needles (27 gauge, for example);
  as a volumizing product with injection using needles which are of larger diameter, from 22 to 26 gauge, for example, and longer (30 to 40 mm, for example); in this case, its cohesive nature will ensure that it stays at the site of injection.

The injectable sterilized aqueous composition according to the invention also finds major application in joint surgery and in dental surgery, for the filling in of periodontal pockets, for example.

These use examples are not in any way limiting, and the injectable sterilized aqueous composition according to the present invention being more broadly envisaged for:
  filling in volumes;
  generating spaces within certain tissues, thus promoting the optimum functioning thereof;
  replacing deficient physiological fluids.

EXAMPLES a) Abbreviations Used
In the examples, the following abbreviations are used:
AL: local anesthetic;
Po: polyol;

CA: additional compound;
ARTI: articaine;
BUPI: bupivacaine;
MEPI: mepivacaine;
PROC: procaine;
ROPI: ropivacaine;
HA: hyaluronic acid;
% G': % change in the elastic component G' compared with the reference composition.

The percentage change in the elastic component G' is defined as being:

% change $G'=100\times(Y-Y')/Y$ with Y=percentage loss of the elastic component G' on sterilization of the reference composition,
and Y'=percentage loss of the elastic component G' on sterilization of the composition tested;
% η: % change in the viscosity η compared with the reference composition.
The percentage change in the viscosity η is defined as being:

% change $\eta=100\times(Z-Z')/Z$ with Z=percentage loss of viscosity 11 on sterilization of the reference composition,
and Z'=percentage loss of viscosity 11 on sterilization of the composition tested;
MAL: maltitol;
MAN: mannitol.

a) Production of Gels
Crosslinked Hyaluronic Acid Gels

The gels comprising crosslinked hyaluronic acid are obtained according to the procedure described in patent application WO 2009/071697 in the name of the applicant, from fibers of sodium hyaluronate (NaHA) and of butanediol diglycidyl ether (BDDE).

Local Anesthetics

The local anesthetics are dissolved in a solution of stabilized phosphate buffer before they are incorporated into the hyaluronic acid gels.

Polyol

The polyol is dissolved in a solution of phosphate buffer before it is incorporated into the hyaluronic acid gels.

Sterilization

The resulting compositions are packaged in syringes which are sterilized by steam autoclaving (T=121° C., 10 min).

c) Rheological Property Measurements

The elastic components G' of the compositions comprising crosslinked hyaluronic acid before and after sterilization by steam autoclaving were measured on a TA Instrument AR 2000 Ex rheometer, in oscillating mode at 25° C., the values of the elastic component G' being recorded at a frequency of 1 Hz.

The viscosity η of the compositions is measured on a TA Instruments AR 2000 Ex rheometer, with applied stress at 25° C. The viscosity value is recorded at a stress of 0.02 s-1, except when specified in the example.

Example 1

Example 1 illustrates the effects of mannitol on the rheological properties during heat sterilization of a gel of hyaluronic acid having a weight-average molecular weight of $3\times10^6$ Da at a concentration of 20 mg/g with a degree of crosslinking X=0.12.

For all the measurements, a reference composition is formulated, replacing the aqueous solution of polyol with an equivalent amount of aqueous solution of phosphate buffer.

TABLE 1

| | AL | | Po | | CA | | | |
|---|---|---|---|---|---|---|---|---|
| N° | nature | [AL] (mg/g) | nature | [Po] (mg/g) | nature | [CA] (mg/g) | [HA]/[AL] | % G' |
| 1 | none | 0 | MAN | 0 | none | 0 | n/a | 0 |
| 2 | none | 0 | MAN | 5 | none | 0 | n/a | 31 |
| 3 | none | 0 | MAN | 35 | none | 0 | n/a | 36 |

In conclusion, the addition of mannitol results in an increase in G' during sterilization by autoclaving. This is in agreement with the effects obtained in the prior art.

Example 2

Example 2 illustrates the effects of various local anesthetics on the rheological properties during heat sterilization of hyaluronic acid gels comprising a polyol.

Example 2-a

Example 2-a illustrates the influence of various local anesthetics on the rheological properties during heat sterilization of a gel of hyaluronic acid having a weight-average molecular weight of $3\times10^6$ Da at a concentration of 20 mg/g with a degree of crosslinking X=0.06, comprising mannitol.

The [HA]/[AL] ratio is 6.67.

The [Po]/[AL] ratio is 11.66.

For all the measurements, a reference composition is formulated, replacing the aqueous solution of local anesthetic within an equivalent amount of aqueous solution of phosphate buffer.

TABLE 2

| | AL | | Po | | CA | | | |
|---|---|---|---|---|---|---|---|---|
| N° | nature | [AL] (mg/g) | nature | [Po] (mg/g) | nature | [CA] (mg/g) | [HA]/[AL] | % G' |
| 4 | none | 0 | MAN | 35 | none | 0 | n/a | 0 |
| 5 | ARTI | 3 | MAN | 35 | none | 0 | 6.67 | −121 |
| 6 | BUPI | 3 | MAN | 35 | none | 0 | 6.67 | −143 |
| 7 | ROPI | 3 | MAN | 35 | none | 0 | 6.67 | −76 |

In conclusion, the addition of articaine, of bupivacaine or of ropivacaine results in a decrease in the G' of the compositions already comprising mannitol, during sterilization by autoclaving. This is particularly surprising if the results obtained by Anteis with regard to lidocaine in application WO 2010/052430 are in particular taken into account.

Example 2-b

Example 2-b illustrates the influence of various local anesthetics on the rheological properties during heat sterilization of a gel of hyaluronic acid having a weight-average molecular weight of $3\times10^6$ Da at a concentration of 20 mg/g with a degree of crosslinking X=0.06, comprising maltitol.

The [HA]/[AL] ratio is 6.67.

The [Po]/[AL] ratio is 11.66.

For all the measurements, a reference composition is formulated, replacing the aqueous solution of local anesthetic with an equivalent amount of aqueous solution of phosphate buffer.

TABLE 3

| N° | AL nature | [AL] (mg/g) | Po nature | [Po] (mg/g) | CA nature | [CA] (mg/g) | [HA]/[AL] | % G' |
|---|---|---|---|---|---|---|---|---|
| 8 | none | 0 | MAL | 35 | none | 0 | n/a | 0 |
| 9 | ARTI | 3 | MAL | 35 | none | 0 | 6.67 | −88 |
| 10 | BUPI | 3 | MAL | 35 | none | 0 | 6.67 | −134 |
| 11 | ROPI | 3 | MAL | 35 | none | 0 | 6.67 | −68 |

In conclusion, the addition of articaine, of bupivacaine or of ropivacaine results in a decrease in the G' of the compositions already comprising maltitol, during the sterilization by autoclaving. This is particularly surprising if the results obtained by Anteis with regard to lidocaine in application WO 2010/052430 are in particular taken into account.

Example 2-c

Example 2-c illustrates the influence of procaine on the rheological properties during heat sterilization of a gel of hyaluronic acid having a weight-average molecular weight of $3 \times 10^6$ Da at a concentration of 20 mg/g with a degree of crosslinking X=0.06, comprising mannitol.

The [HA]/[AL] ratio is 6.67.
The [Po]/[AL] ratio is 11.66.

For all the measurements, a reference composition is formulated, replacing the aqueous solution of local anesthetic with an equivalent amount of aqueous solution of phosphate buffer.

TABLE 4

| N° | AL nature | [AL] (mg/g) | Po nature | [Po] (mg/g) | CA nature | [CA] (mg/g) | [HA]/[AL] | % G' |
|---|---|---|---|---|---|---|---|---|
| 12 | none | 0 | MAN | 35 | none | 0 | n/a | 0 |
| 13 | PROC | 3 | MAN | 35 | none | 0 | 6.67 | −12 |

In conclusion, the addition of procaine results in a decrease in the G' of the compositions already comprising mannitol, during the sterilization by autoclaving. This is particularly surprising if the results obtained by Anteis with regard to lidocaine in application WO 2010/052430 are in particular taken into account.

Examples 2-a, 2-b and 2-c illustrate that the addition of at least one local anesthetic chosen from the group consisting of benzocaine, chloroprocaine, procaine, etidocaine, aptocaine, chlorobutanol, diamocaine, dyclonine, guafecainol, polidocanol, mepivacaine, prilocaine, articaine, bupivacaine, ropivacaine, tetracaine and salts thereof and isolated isomers thereof results in a decrease in the G' of compositions already comprising at least one polyol, during sterilization by autoclaving.

Example 2-D

Example 2-d illustrates the influence of mepivacaine on the rheological properties during heat sterilization of a gel of non-crosslinked hyaluronic acid having a weight-average molecular weight of $3 \times 10^6$ Da at a concentration of 20 mg/g, comprising mannitol.

The [HA]/[AL] ratio ranges from 20 to 2.

For all the measurements, a reference composition is formulated, replacing the aqueous solution of local anesthetic with an equivalent amount of aqueous solution of phosphate buffer.

TABLE 5

| N° | AL nature | [AL] (mg/g) | Po nature | [Po] (mg/g) | CA nature | [CA] (mg/g) | [HA]/[AL] | % η |
|---|---|---|---|---|---|---|---|---|
| 14 | none | 0 | MAN | 35 | none | 0 | n/a | 0 |
| 15 | MEPI | 1 | MAN | 35 | none | 0 | 20 | −43 |
| 16 | MEPI | 3 | MAN | 35 | none | 0 | 6.67 | −62 |
| 17 | MEPI | 6 | MAN | 35 | none | 0 | 3.33 | −67 |
| 18 | MEPI | 10 | MAN | 35 | none | 0 | 2 | −68 |

In conclusion, the addition of mepivacaine results in a decrease in the q of the compositions based on non-crosslinked hyaluronic acid already comprising mannitol, during sterilization by autoclaving.

Example 3

Example 3 illustrates the influence of mepivacaine on the rheological properties during heat sterilization of a gel of hyaluronic acid having a weight-average molecular weight of $3 \times 10^6$ Da at a concentration of 20 mg/g with a degree of crosslinking X=0.06, comprising mannitol.

The [HA]/[AL] ratio is 6.67.
The [Po]/[AL] ratio is 11.66.

For all the measurements, a reference composition is formulated, replacing the aqueous solution of local anesthetic with an equivalent amount of aqueous solution of phosphate buffer.

TABLE 6

| N° | AL nature | [AL] (mg/g) | Po nature | [Po] (mg/g) | CA nature | [CA] (mg/g) | [HA]/[AL] | % G' | F(N) 13 mm/min 27 G1/2 | η $0.017^{s-1}$ (Pa·s) | η $1000^{s-1}$ (Pa·s) |
|---|---|---|---|---|---|---|---|---|---|---|---|
| 19 | none | 0 | MAN | 35 | none | 0 | n/a | 0 | 21 | 3057 | 1.4 |
| 20 | MEPI | 3 | MAN | 35 | none | 0 | 6.67 | −109 | 20 | 2538 | 1.3 |

In conclusion, the addition of mepivacaine results in a decrease in the G' of the compositions already comprising mannitol, during sterilization by autoclaving. This is particularly surprising if the results obtained by Anteis with regard to lidocaine in application WO 2010/052430 are in particular taken into account.

Furthermore, the addition of mepivacaine results in a decrease in the viscosity at low shear rate ($0.017^{s-1}$), but not at high shear rate ($1000^{s-1}$). Thus, the injectability (linked to the viscosity at high shear rate) is not significantly modified.

What is claimed is:
1. An injectable sterilized aqueous composition comprising:
   at least one hyaluronic acid,
   at least one polyol chosen from the group consisting of glycerol, sorbitol, propylene glycol, xylitol, mannitol, erythritol, maltitol and lactitol, alone or as a mixture, and at least one local anesthetic chosen from the group consisting of benzocaine, chloroprocaine, procaine, etidocaine, aptocaine, chlorobutanol, diamocaine, dyclonine, guafecainol, polidocanol, mepivacaine, prilocaine, articaine, bupivacaine, ropivacaine, tetracaine and salts thereof and isolated isomers thereof; wherein magnesium ascorbyl phosphate (MAP) and sucrose octasulfate (SOS) are not present in the injectable sterilized aqueous composition.

2. The injectable sterilized aqueous composition as claimed in claim 1, which comprises at least one non-crosslinked hyaluronic acid or a salt thereof, alone or as a mixture.

3. The injectable sterilized aqueous composition as claimed in claim 1, which comprises at least one crosslinked hyaluronic acid or a salt thereof, alone or as a mixture.

4. The injectable sterilized aqueous composition as claimed in claim 1, wherein the concentration of the at least one hyaluronic acid [HA] is between 2 mg/g and 50 mg/g of total weight of said composition.

5. The injectable sterilized aqueous composition as claimed in claim 1, wherein the concentration of the at least one hyaluronic acid [HA] is 20 mg/g of total weight of said composition.

6. The injectable sterilized aqueous composition as claimed in claim 5, wherein the concentration of the at least one polyol [Po] is between 0.01 mg/g and 50 mg/g.

7. The injectable sterilized aqueous composition as claimed in claim 5, wherein the concentration of the at least one local anesthetic [AL] is between 0.01 mg/g and 50 mg/g.

8. The injectable sterilized aqueous composition as claimed in claim 5, wherein the weight ratio between the concentration of the at least one polyol [Po] and the concentration of the at least one local anesthetic [AL]:[Po]/[AL] is between 0.0002 and 5000; $0.0002 \leq [Po]/[AL] \leq 5000$.

9. The injectable sterilized aqueous composition as claimed in claim 5, wherein the weight ratio between the concentration of the at least one hyaluronic acid [HA] and the concentration of the at least one local anesthetic [AL]:[HA]/[AL] is between 0.1 and 50; $0.1 \leq [HA]/[AL] \leq 50$.

10. The injectable sterilized aqueous composition as claimed in claim 5, wherein the sterilization is carried out by heat, moist heat, gamma ($\gamma$) radiation, or by accelerated electron beam.

11. The injectable sterilized aqueous composition as claimed in claim 5, which further comprises at least one additional compound.

12. A process for producing an injectable sterilized aqueous composition as claimed in claim 5, which comprises at least the following steps:
   1) a step of hydration in a buffer solution at a pH close to physiological pH of the fibers of at least one hyaluronic acid or a salt thereof, alone or as a mixture, so as to obtain a hydrogel;
   2) a step of incorporation of at least one polyol in aqueous solution into the hydrogel obtained in the previous step;
   3) a step of incorporation of at least one local anesthetic chosen from the group consisting of benzocaine, chloroprocaine, procaine, etidocaine, aptocaine, chlorobutanol, diamocaine, dyclonine, guafecainol, polidocanol, mepivacaine, prilocaine, articaine, bupivacaine, ropivacaine and tetracaine and salts thereof and isolated isomers thereof, into the hydrogel obtained in the previous step;
   4) a homogenization step; and
   5) a sterilization step;
it being possible for said steps 2) and 3) to be carried out in any order or simultaneously.

13. The production process as claimed in claim 12, which further comprises at least one crosslinking step simultaneously with or subsequent to step 1.

14. A kit comprising an injectable sterilized aqueous composition as claimed in claim 1, packaged in syringes and sterilized after packaging.

* * * * *